(12) United States Patent
Hu

(10) Patent No.: US 6,821,991 B2
(45) Date of Patent: Nov. 23, 2004

(54) 2-SUBSTITUTED THIAZOLIDINONES AS β-3 ADRENERGIC RECEPTOR AGONISTS

(75) Inventor: Baihua Hu, Audubon, PA (US)

(73) Assignee: Wyeth, Madison, WI (US)

( * ) Notice: Subject to any disclaimer, the term of this patent is extended or adjusted under 35 U.S.C. 154(b) by 0 days.

(21) Appl. No.: 10/440,788

(22) Filed: May 19, 2003

(65) Prior Publication Data

US 2003/0176412 A1 Sep. 18, 2003

Related U.S. Application Data

(62) Division of application No. 10/132,483, filed on Apr. 25, 2002, now Pat. No. 6,583,140, which is a division of application No. 09/904,157, filed on Jul. 12, 2001, now Pat. No. 6,410,734.
(60) Provisional application No. 60/218,724, filed on Jul. 17, 2000.

(51) Int. Cl.[7] .................... A61K 31/445; A61K 31/426; C07D 413/10; C07D 417/10; C07D 277/08
(52) U.S. Cl. ................ 514/329; 514/369; 514/376; 544/133; 544/369; 546/209; 548/184; 548/225; 548/953
(58) Field of Search ............ 546/209; 514/329, 514/369, 376; 548/953, 225, 184; 544/133, 369

(56) References Cited

U.S. PATENT DOCUMENTS

| | | |
|---|---|---|
| 4,526,786 A | 7/1985 | Bourgery et al. |
| 4,813,998 A | 3/1989 | Van Lommen et al. |
| 5,153,210 A | 10/1992 | Ainsworth et al. |
| 5,561,142 A | 10/1996 | Fisher et al. |
| 5,578,620 A | 11/1996 | Fujita et al. |
| 5,614,523 A | 3/1997 | Audia et al. |
| 5,741,789 A | 4/1998 | Hibschman |
| 5,786,356 A | 7/1998 | Bell et al. |
| 5,789,402 A | 8/1998 | Audia et al. |
| 5,998,452 A | 12/1999 | Ohi et al. |
| 6,069,176 A | 5/2000 | Tsuchiya et al. |
| 6,150,378 A | 11/2000 | Chatterjee et al. |
| 6,288,231 B1 | 9/2001 | Chatterjee et al. |
| 6,346,532 B1 | 2/2002 | Maruyama et al. |
| 6,395,762 B1 | 5/2002 | Fobare et al. |
| 6,410,734 B1 | 6/2002 | Hu |
| 6,444,685 B1 | 9/2002 | Sum et al. |
| 6,451,814 B1 | 9/2002 | Ashwell et al. |
| 6,458,817 B1 | 10/2002 | Quagliato et al. |
| 6,465,501 B2 | 10/2002 | Malamas et al. |
| 6,498,170 B2 | 12/2002 | Sum et al. |
| 6,506,901 B2 | 1/2003 | Steffan et al. |
| 6,509,358 B2 | 1/2003 | Fobare et al. |
| 6,514,991 B2 | 2/2003 | Coghlan et al. |
| 6,525,202 B2 | 2/2003 | Hu et al. |
| 6,537,994 B2 | 3/2003 | Ashwell et al. |

FOREIGN PATENT DOCUMENTS

| | | |
|---|---|---|
| EP | 0 089 154 A2 | 9/1983 |
| EP | 0 236 624 A2 | 9/1987 |
| EP | 0 449 261 A1 | 10/1991 |
| EP | 0 590 793 A1 | 4/1994 |
| EP | 0 659 737 A2 | 6/1995 |
| EP | 0 714 883 A1 | 6/1996 |
| EP | 0 764 640 A1 | 3/1997 |
| EP | 0 801 060 A1 | 10/1997 |
| FR | 2 798 126 A1 | 3/2001 |
| GB | 2 163 150 A | 2/1986 |
| WO | WO 95/29159 A1 | 11/1995 |
| WO | WO 97/41120 | 11/1997 |
| WO | WO 97/46556 A1 | 12/1997 |
| WO | WO 98/22480 A1 | 5/1998 |
| WO | WO 98/32753 A1 | 7/1998 |
| WO | WO 99/65895 | 12/1999 |
| WO | WO 99/65895 A1 | 12/1999 |
| WO | WO 01/17989 A2 | 3/2001 |
| WO | WO 01/43744 A1 | 6/2001 |
| WO | WO 01/44227 A1 | 6/2001 |

OTHER PUBLICATIONS

Marc S. Berridge et al., Nucl. Med. Biol., 1992, 563–569, 19(5).
Joan M. Caroon et al., J. Pharm. Sci., Jan. 1987, 32–34, 76(1).
A. Guy et al., Synthesis, Sep. 1992, 821–22.
Manabu Hori et al., J. Org. Chem., 1998, 889–894, 63.
Yunsheng Huang et al., J. Med. Chem., 1998, 2361–2370, 41.
Bernard Hulin et al., J. Med. Chem., 1992, 1853–1864, 35.
Carl Kaiser et al., J. Med. Chem., 1977, 687–692, 20(5).
Yutaka Kawashima et al., Chem. Pharm. Bull, 1995, 1132–1136, 43(7).

(List continued on next page.)

Primary Examiner—Golam M M Shameem
(74) Attorney, Agent, or Firm—Kimberly R. Hild

(57) ABSTRACT

This invention provides compounds of Formula I having the structure

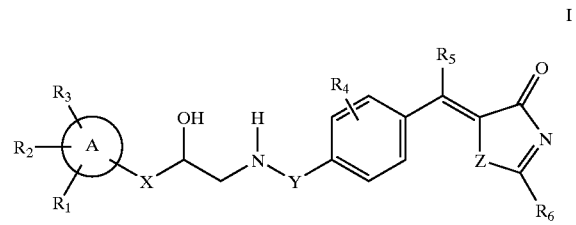

wherein:
A, X, Y, Z, $R_1$, $R_2$, $R_3$, $R_4$, $R_5$, and $R_6$ are as defined hereinbefore or a pharmaceutically acceptable salt thereof, which are useful in treating or inhibiting metabolic disorders related to insulin resistance or hyperglycemia (typically associated with obesity or glucose intolerance), atherosclerosis, gastrointestinal disorders, neurogenetic inflammation, and frequent urination; and are particularly useful in the treatment or inhibition of type II diabetes.

5 Claims, No Drawings

OTHER PUBLICATIONS

Kiyoto Koguro et al., Synthesis, 1998, 910–914.
Gerard Leclerc et al., J. Med. Chem., 1980, 738–744, 23(7).
D. Mauleon et al., Il Farmaco,1989, 1109–1117, 44(11).
Alexander McKillop et al., J. Am. Chem. Soc., Sep. 1971, 4919–4920, 93(19).
Ricardo Tapia et al., Synthetic Communications, 1986, 681–687, 16(6).
Edward C. Taylor et al., Synthesis, Aug. 1981, 606–608.
Michiaki Tominaga et al., Chem. Pharm. Bull, 1987, 3699–3704, 35(9).
R.H. Uloth et al., J. Med. Chem., 1966, 88–97, 9.
Paul C. Unangst et al., J. Med. Chem., 1994, 322–328, 37.
Sophie Vanwetswinkel et al., J. Anitbiotics, Sep. 1994, 1041–1051, 47(9).

S. Tamada et al., JP 01061468 A2 (English abstract), 1989.
Baihua Hu, Bioorganic & Medicinal Chemistry Letters, 11 (2001) 981–984.
Ann Weber et al., Bioorg. & Med. Chem. Letters, 1998, 1101–1106, 8.
K. Anji Reddy et al., Bioorg. & Med. Chem. Letters, 1998, 999–1002, 8.
Barrie Cantello et al., J. Med. Chem., 1994, 3977–3985, 37.
Abstract of WO 99/25687A1, Accession No. 1999:350651 Caplus (1999).
Baihua Hu et al., J. Med. Chem., 44, 1456–1466 (2001).
Abstracts of Papers American Chemical Society, 221, 1–2, (2001).

2-SUBSTITUTED THIAZOLIDINONES AS β-3 ADRENERGIC RECEPTOR AGONISTS

This application is a divisional of U.S. application Ser. No. 10/132,483, filed Apr. 25, 2002 now U.S. Pat. No. 6,583,140, which is a divisional of U.S. application Ser. No. 09/904,157, filed Jul. 12, 2001, now U.S. Pat. No. 6,410,734. The '157 application claims the benefit of U.S. Provisional Application No. 60/218,724, filed Jul. 17, 2000.

BACKGROUND OF THE INVENTION

This invention relates to 2-substituted thiazolidinone derivatives which are $\beta_3$ adrenergic receptor agonists useful for the treatment of metabolic disorders related to insulin resistance or hyperglycemia (typically associated with obesity or glucose intolerance), atherosclerosis, gastrointestinal disorders, neurogenetic inflammation, and frequent urination, and are particularly useful in the treatment or inhibition of type II diabetes.

The subdivision of β adrenergic receptors (β-AR) into $\beta_1$- and $\beta_2$-AR has led to the development of $\beta_1$- and $\beta_2$-antagonists and/or agonists which have been useful for the treatment of cardiovascular disease and asthma. The recent discovery of "atypical" receptors, later called $\beta_3$-AR, has led to the development of $\beta_3$-AR agnoists which may be potentially useful as antiobesity and antidiabetic agents. For recent reviews on $\beta_3$-AR agnoists, see: 1. A. D. Strosberg, Annu. Rev. *Pharmacol. Toxicol.* 1997, 37,421; 2. A. E. Weber, *Ann. Rep. Med. Chem.* 1998, 33, 193; 3. C. P. Kordik and A. B. Reitz, *J. Med. Chem.* 1999, 42, 181; 4. C. Weyer, J. F. Gautier and E. Danforth, *Diabetes and Metabolism*, 1999, 25, 11.

Compounds that are potent and selective $\beta_3$ agonists, may be potentially useful antiobesity agents. Low levels or lack of $\beta_1$ and $\beta_2$-agonistic properties will minimize or eliminate the adverse side effects that are associated with $\beta_1$ and $\beta_2$ agonistic activities, i.e. increased heart rate, and muscle tremor, respectively. Early developments in the $\beta_3$-agonist field are described in European patent 427480, U.S. Pat. Nos. 4,396,627, 4,478,849, 4,999,377, 5,153,210. Although the early developments purport to claim compounds with greater $\beta_3$-AR selectivity over the $\beta_1$- and $\beta_2$-AR. However, clinical trials in humans with those early developed $\beta_3$-agonists have, so far, not been successful.

More recently, potent and selective human $\beta_3$ agonists have been described in several patents and published applications: WO 98/32753, WO 97/46556, WO 97/37646, WO 97/15549, WO 97/25311, WO 96/16938, WO 95/29159, European Patents 659737, 801060, 714883, 764640, 827746, and U.S. Pat. Nos. 5,561,142, 5,705,515, 5,436,257, and 5,578,620. These compounds were evaluated in Chinese hamster ovary (CHO) cells test procedures, expressing cloned human $\beta_3$ receptors, which predict the effects that can be expected in humans (Granneman et al., *Mol Pharmacol.*, 1992, 42, 964; Emorine et al., *Science*, 1989, 245, 1118; Liggett *Mol. Pharmacol.*, 1992, 42, 634).

$\beta_3$-Adrenergic agonists also are useful in controlling the frequent urge of urination. It has been known that relaxation of the bladder detrusor is under beta adrenergic control (Li J H, Yasay G D and Kau S T *Pharmacology* 1992; 44: 13–18). Beta-adrenoceptor subtypes are in the detrusor of guinea-pig urinary bladder. Recently, a number of laboratories have provided experimental evidence of $\beta_3$ adrenergic receptors in a number of animal species including human (Yamazaki Y, Takeda H, Akahane M, Igawa Y, et al. Br. *J. Pharmacol.* 1998; 124: 593–599), and that activation of the $\beta_3$ receptor subtype by norepinephrine is responsible for relaxation of the urinary bladder.

Urge urinary incontinence is characterized by abnormal spontaneous bladder contractions that can be unrelated to bladder urine volume. Urge urinary incontinence is often referred to hyperactive or unstable bladder. Several etiologies exist and fall into two major categories, myogenic and neurogenic. The myogenic bladder is usually associated with detrusor hypertrophy secondary to bladder outlet obstruction, or with chronic urinary tract infection. Neurogenic bladders are associated with, an uninhibited micturition reflex. An upper motor neuron disease is usually the underlying cause. In either case, the disease is characterized my abnormal spontaneous contractions that result in an abnormal sense of urinary urgency and involuntary urine loss. At present, the most common therapy for hyperactive bladder includes the use of antimuscarinic agents to block the action of the excitatory neurotransmitter acetylcholine. While effective in neurogenic bladders, their utility in myogenic bladders is questionable. In addition, due to severe dry mouth side-effects associated with antimuscarinic therapy, the patient compliance with these agents is only approximately 30%.

In the bladder, $\beta_3$ adrenergic receptor agonists activate adenylyl cyclase and generate cAMP through the G-protein coupled $\beta_3$ receptor. The resulting phosphorylation of phospholamban/calcium ATPase enhances uptake of calcium into the sarcoplasmic reticulum. The decrease in intracellular calcium inhibits bladder smooth muscle contractility.

It is suggested therefore, that activation of the $\beta_3$ adrenergic receptor in the urinary bladder will inhibit abnormal spontaneous bladder contractions and be useful for the treatment of bladder hyperactivity. Note, that unlike the antimuscarinics, $\beta_3$ adrenergic receptor agonists would be expected to be active against both neurogenic and myogenic etiologies.

Despite all these recent developments there is still no single therapy available for the treatment of type II diabetes (NIDDM), obesity, atherosclerosis, gastrointestinal disorders, neurogenetic inflammation, frequent urination and related diseases. A potent and selective $\beta_3$ adrenergic receptor agonist is therefore highly desirable for the potential treatment of such disease states.

DESCRIPTION OF THE INVENTION

This invention provides compounds of Formula I having the structure

I

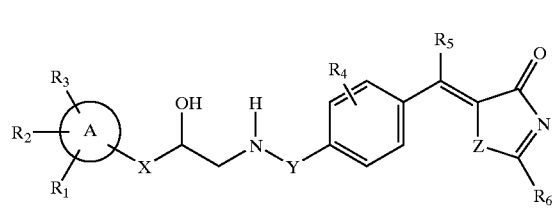

wherein:

A is aryl or Het;

X is —OCH$_2$—, —SCH$_2$—, or a bond;

Y is alkyl of 1–6 carbon atoms, alkyloxy of 1–6 carbon atoms, azetidine, pyrrolidine or piperidine; wherein the nitrogen of the azetidine, pyrrolidine or piperidine attached to the adjacent phenyl ring;

Z is S, O, NH or N-alkyl of 1–6 carbon atoms;

$R_1$, $R_2$, and $R_3$ are each, independently, hydrogen, alkyl of 1–6 carbon atoms, cycloalkyl of 3–8 carbon atoms, hydroxy, halogen, trifluoromethyl, alkoxy of 1–6 carbon atoms, benzyloxy, allyloxy, propargyloxy, acyloxy of 2–7 carbon atoms, cyano, nitro, amino, aminocarbonyl, alkylamino of 1–6 carbon atoms, dialkylamino of 1–6 carbon atoms per alkyl group, formamido, ureido, acylamino of 2–7 carbon atoms, alkylsulfonylamino of 1–6 carbon atoms, arylsulfonylamino, dialkyloxyphosphorylamino of 1–6 carbon atoms per alkyl group, or dihydroxyphosphorylamino, or two of the three substituents ($R_1$, $R_2$ and $R_3$) combine with the carbon to which each is attached to form a aryl fused cycloalkyl of 3–8 carbon atoms optionally substituted with acylamino or hydroxy;

$R_4$ is hydrogen, alkyl of 1–6 carbon atoms, alkoxy of 1–6 carbon atoms, hydroxy, carboxy, or halogen;

$R_5$ is hydrogen or alkyl of 1–6 carbon atoms;

$R_6$ is (i) $SCH_3$ or $NR_7R_8$; (ii) an amino acid, wherein the nitrogen of amino acid is attached to the adjacent thiazolidinone, oxazolidinone, or imidazolidinone ring; (iii) an alkyl ester of an amino acid, wherein the nitrogen of amino acid is attached to the adjacent thiazolidinone, oxazolidinone, or imidazolidinone ring, and the alkyl moiety of the alkyl ester contains 1–6 carbon atoms; or (iv) $NH(C=Q)NR_7R_8$ or $NHNH(C=Q)NR_7R_8$;

$R_7$ and $R_8$ are each, independently, hydrogen, aryl, Het, alkyl of 1–6 carbon atoms, arylalkyl in which the alkyl moiety has 1–6 carbon atoms, Hetalkyl in which the alkyl moiety has 1–6 carbon atoms, haloalkyl of 1–6 carbon atoms, dialkylaminoalkyl of 1–6 carbon atoms per alkyl group, hydroxy, alkoxy of 1–6 carbon atoms, benzyloxy, cyano, alkylamino of 1–6 carbon atoms, dialkylamino having 1–6 carbon atoms per alkyl group, acylamino of 2–7 carbon atoms, alkylsulfonylamino of 1–6 carbon atoms; or $R_7$ and $R_8$ are taken together with the nitrogen to which each is attached to form a saturated, unsaturated, or partially unsaturated 3–8 membered heterocyclic ring optionally containing 1 to 3 additional heteroatoms selected from S, O, and N, and optionally substituted with $R_9$;

Q is O, S, NH, NCN; or Q and one of $R_7$ and $R_8$ are taken together to form a partially unsaturated or unsaturated 3–8 membered heterocyclic ring optionally containing 1–2 additional heteroatoms selected from S, O, and N, and optionally substituted with $R_9$;

Het is a monocyclic or bicyclic heterocycle of 5–10 ring atoms, having 1–4 heteroatoms selected from oxygen, nitrogen, and sulfur; wherein the heterocycle may be saturated, unsaturated, or partially unsaturated; may be optionally fused to a phenyl ring, and may be optionally substituted with $R_9$;

$R_9$ is alkyl of 1–6 carbon atoms, cycloalkyl of 3–8 carbon atoms, arylalkyl having 1–6 carbon atoms in the alkyl group, hydroxy, halogen, trifluoromethyl, alkoxy of 1–6 carbon atoms, benzyloxy, allyloxy, propargyloxy, acyloxy of 2–7 carbon atoms, cyano, nitro, amino, aminocarbonyl, alkylamino of 1–6 carbon atoms, dialkylamino of 1–6 carbon atoms per alkyl group, formamido, ureido, acylamino of 2–7 carbon atoms, alkylsulfonylamino of 1–6 carbon atoms, arylsulfonylamino, dialkyloxyphosphorylamino of 1–6 carbon atoms per alkyl group, or dihydroxyphosphorylamino;

or a pharmaceutically acceptable salt thereof, which are selective agonists at human $\beta_3$ adrenergic receptors and are useful in treating or inhibiting metabolic disorders related to insulin resistance or hyperglycemia (typically associated with obesity or glucose intolerance), atherosclerosis, gastrointestinal disorders, neurogenetic inflammation, and frequent urination; and are particularly useful in the treatment or inhibition of type II diabetes.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, such as alkali metal salts (for example, sodium, lithium, or potassium), alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when a compound of this invention contains an acidic moiety.

Alkyl includes both straight chain as well as branched moieties. By definition alkyl also includes alkyl moieties which are optionally mono- or poly substituted with groups such as halogen, hydroxy, cyano, alkoxy, aryloxy, arylalkyl, alkylthio, arylthio, amino, alkylamino, and dialkylamino. Halogen means bromine, chlorine, fluorine, and iodine. Where a substituent contains one or more moieties which have the same designation, each of the moieties can be the same or different.

Preferred aryl moieties include phenyl or naphthyl. Preferred Het moieties include: (a) 6-membered saturated, partially unsaturated, or unsaturated heterocycles containing 1–2 nitrogens, optionally fused to a phenyl ring; (b) 5-membered saturated, partially saturated, or unsaturated heterocycles containing 1–3 nitrogen, oxygen, or sulfur atoms, optionally fused to a phenyl ring; (c) saturated, partially unsaturated, or unsaturated bicyclic heterocycles containing 1–4 nitrogen, oxygen, or sulfur atoms; (d) carbazole, dibenzofuran, and dibenzothiophene. In the Het of categories (a), (b), and (c), ring carbon atoms may be carbonyl moieties, where the ring does not contain a double bond in that position (for example, thiazolidine-2,4-dione).

More preferred Het rings include pyrrole, furan, thiophene, imidazole, pyrazole, furazan, triazole, tetrazole, oxazoel, oxadiazole, isoxazole, thiazole, isothiazole, thiadiazole, pyridine, pyrimidine, pyridazine, pyrazine, 1,3,5-triazine, 1,2,4,5-tetrazine, benzofuran, isobenzofuran, indole, isoindole, benzothiophene, benzimidazol, 3H-benzoxazol-2-one, benzotriazole, quinoline, isoquinoline, quinazoline, indazole, 1H-quinolin-2-one, 3,4-dihydro-1H-quinolin-2-one, 2,3-dihydro-1H-indole, 1,3-dihydro-benzoimidazol-2-one, 1,3-dihydro-benzoimidazol-2-thione, and carbazole. It is understood that Het do not contain heteroatoms in arrangements which would make them inherently unstable. For example, the term Het does not include ring systems containing O—O bonds in the ring backbone.

Preferred amino acids include alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine, histidine, β-alanine, cyclopropane amino acids (such as 1-aminocyclopropane-1-carboxylic acid, allo-coronamic acid and 2,3-methanohomoserine), 1-aminocyclohexane-1-carboxylic acid, isonipecotic acid, 2-azetidinecarboxylic acid.

The compounds of the present invention contain at least one asymmetric center. Additional asymmetric centers may exist on the molecule depending upon the structure of the substituents on the molecule. The compounds may be prepared as a racemic mixture and can be used as such, or may be resolved into all individual steroisomers. In addition to covering the racemic compounds, this invention also covers all individual isomers, enantiomers, diasteromers or mixtures thereof, regardless of whether the structural representations of the compounds indicate such stereochemistry.

The compounds of the present invention may also contain geometric isomers. Thus, the present invention includes all individual isomers and mixtures thereof.

Preferred compounds of Formula I are those in which

A is phenyl or Het;

X is —OCH$_2$—, or a bond;

Y is alkyl of 1–6 carbon atoms, alkyloxy of 1–6 carbon atoms, or piperidine;

Z is S, O, NH or N-alkyl of 1–6 carbon atoms;

$R_1$, $R_2$, and $R_3$ are each, independently, hydrogen, alkyl of 1–6 carbon atoms, hydroxy, halogen, trifluoromethyl, alkoxy of 1–6 carbon atoms, acyloxy of 2–7 carbon atoms, cyano, nitro, amino, aminocarbonyl, alkylamino of 1–6 carbon atoms, dialkylamino of 1–6 carbon atoms per alkyl group, formamido, ureido, acylamino of 2–7 carbon atoms, or alkylsulfonylamino of 1–6 carbon atoms;

$R_4$ is hydrogen;

$R_5$ is hydrogen;

$R_6$ is (i) NR$_7$R$_8$; (ii) an amino acid, wherein the nitrogen of amino acid attached to the adjacent thiazolidinone, oxazolidinone, or imidazolidinone ring; (iii) an alkyl ester of an amino acid, wherein the nitrogen of amino acid attached to the adjacent thiazolidinone, oxazolidinone, or imidazolidinone ring, and the alkyl moiety of the alkyl ester contains 1–6 carbon atoms; or (iv) NH(C=Q)NR$_7$R$_8$;

$R_7$ and $R_8$ are each, independently, hydrogen, Het, alkyl of 1–6 carbon atoms, Hetalkyl in which the alkyl moiety has 1–6 carbon atoms, dialkylaminoalkyl of 1–6 carbon atoms per alkyl group, cyano, hydroxy, or alkylamino of 1–6 carbon atoms; or $R_7$ and $R_8$ are taken together with the nitrogen to which each is attached to form a saturated, unsaturated, or partially unsaturated 3–8 membered heterocyclic ring optionally containing 1 to 3 additional heteroatoms selected from S, O and N, and optionally substituted with $R_9$;

Q is O, S, NH, NCN;

Het is (a) a 6-membered saturated, partially unsaturated, or unsaturated heterocycle containing 1–2 nitrogens, optionally fused to a phenyl ring; (b) a 5-membered saturated, partially saturated, or unsaturated heterocycle containing 1–3 nitrogen, oxygen, or sulfur atoms, optionally fused to a phenyl ring; (c) a saturated, partially unsaturated, or unsaturated bicyclic heterocycle containing 1–4 nitrogen, oxygen, or sulfur atoms; (d) carbazole, dibenzofuran, and dibenzothiophene; wherein one or more of the ring carbon atoms of Het as described in (a), (b), or (c) may be a carbonyl moiety, where the ring does not contain a double bond in the position corresponding to that carbon atom; wherein Het may be optionally substituted by $R_9$;

$R_9$ is alkyl of 1–6 carbon atoms, or arylalkyl having 1–6 carbon atoms in the alkyl group;

or a pharmaceutically acceptable salt thereof.

Specifically preferred compounds of this invention are:

a) 4-((2S)-2-hydroxy-3-{1-[4-(2-methylamino-4-oxo-4H-thiazol-5-ylidenemethyl)-phenyl]-piperidin-4-ylamino}-propoxy)-1,3-dihydro-benzoimidazol-2-one;

b) 4-[(2S)-2-hydroxy-3-(1-{4-[2-(2-morpholin-4-yl-ethylamino)-4-oxo-4H-thiazol-5-ylidenemethyl]-phenyl}-piperidin-4-ylamino)-propoxy]-1,3-dihydro-benzoimidazol-2-one;

c) 4-[(2S)-3-(1-{4-[2-(1-benzyl-piperdin-4-ylamino)-4-oxo-4H-thiazol-5-ylidenemethyl]-phenyl}-piperidin-4-ylamino)-2-hydroxy-propoxy]-1,3-dihydro-benzoimidazol-2-one;

d) 2-(1-benzyl-piperidin-4-ylamino)-5-(4-{(2S)-4-[2-hydroxy-3-(4-hydroxy-phenoxy)-propylamino]-piperidin-1-yl}-benzylidene)-thiazol-4-one;

e) N-{5-[2-(1-{4-[2-(1-benzyl-piperidin-4-ylamino)-4-oxo-4H-thiazol-5-ylidenemethyl]-phenyl}-piperidin-4-ylamino)-1-hydroxy-ethyl]-2-hydroxy-phenyl}-methanesulfonamide;

f) N'-[5-(4-{4-[(2S)-2-hydroxy-3-(2-oxo-2,3-dihydro-1H-benzoimidazol-4-yloxy)-propylamino]-piperidin-1-yl}-benzylidene)-4-oxo-4,5-dihydro-thiazol-2-yl]-N,N-dimethyl-guanidine;

g) N-{5-[2-(1-{4-[2-(N',N'-dimethyl-guanidino)-4-oxo-4H-thiazol-5-ylidenemethyl]-phenyl}-piperidin-4-ylamino)-1-hydroxy-ethyl]-2-hydroxy-phenyl}methanesulfonamide;

h) 3-[5-(4-{4-[(2S)-2-hydroxy-3-(2-oxo-2,3-dihydro-1H-benzoimidazol-4-yloxy)-propylamino]-piperidin-1-yl}-benzylidene)-4-oxo-4,5-dihydro-thiazol-2-ylamino]-propionic acid ethyl ester;

i) 3-[5-(4-{4-[(2S)-2-hydroxy-3-(2-oxo-2,3-dihydro-1H-benzoimidazol-4-yloxy)-propylamino]-piperidin-1-yl}-benzylidene)-4-oxo-4,5-dihydro-thiazol-2-ylamino]-propionic acid;

j) 4-((2S)-2-hydroxy-3-{1-[4-(2-hydroxyamino-4-oxo-4H-thiazol-5-ylidenemethyl)-phenyl]-piperidin-4-ylamino}-propoxy)-1,3-dihydro-benzoimidazol-2-one;

k) N-[2-hydroxy-5-(1-hydroxy-2-{1-[4-(2-hydroxyamino-4-oxo-4H-thiazol-5-ylidenemethyl)-phenyl]-piperidin-4-ylamino}-ethyl)-phenyl]-methanesulfonamide;

l) 4-((2S)-2-hydroxy-3-{1-[4-(4-oxo-2-piperidin-1-yl-4H-thiazol-5-ylidenemethyl)-phenyl]-piperidin-4-ylamino}-propoxy)-1,3-dihydro-benzoimidazol-2-one;

m) N-[2-hydroxy-5-((1R)-1-hydroxy-2-{1-[4-(4-oxo-2-piperidin-1yl-4H-thiazol-5-ylidenemethyl)-phenyl]-piperidin-4-ylamino}-ethyl)-phenyl]-methanesulfonamide;

n) N-[2-hydroxy-5-((2S)-2-hydroxy-3-{1-[4-(4-oxo-2-piperidin-1-yl-4H-thiazol-5-ylidenemethyl)-phenyl]-piperidin-4-ylamino}-propoxy)-phenyl]-methanesulfonamide;

o) 8-hydroxy-5-((2S)-2-hydroxy-3-{1-[4-(4-oxo-2-piperidin-1-yl-4H-thiazol-5-ylidenemethyl)-phenyl]-piperidin-4-ylamino}-propoxy)-3,4-dihydro-1H-quinolin-2-one;

p) 5-(4-{4-[(2S)-2-hydroxy-3-(4-hydroxy-phenoxy)-propylamino]-piperidin-1-yl}-benzylidene)-2-piperidin-1-yl-thiazol-4-one;

q) N'-[5-(4-{4-[(2S)-2-hydroxy-3-(8-hydroxy-2-oxo-1,2,3,4-tetrahydro-quinolin-5-yloxy)-propylamino]- piperidin-1-yl}-benzylidene)-4-oxo-4,5-dihydro-thiazol-2-yl]-N,N-dimethyl-guanidine;

r) 4-((2S)-2-hydroxy-3-{1-[4-(2-morpholin-4-yl-4-oxo-4H-thiazol-5-ylidenemethyl)-phenyl]-piperidin-4-ylamino}-propoxy)-1,3-dihydro-benzoimidazol-2-one;

s) 4-[(2S)-2-hydroxy-3-(1-{4-[2-(4-methyl-piperidin-1-yl)-4-oxo-4H-thiazol-5ylidenemethyl]-phenyl}-piperidin-4-ylamino)-propoxy]-1,3-dihydro-benzoimidazol-2-one;

t) N'-(5-{4-[4-((2S)-2-hydroxy-3-phenoxy-propylamino)-piperidin-1-yl]-benzylidene}-4-oxo-4,5-dihydro-thiazol-2-yl)-N,N-dimethyl-guanidine;

u) N'-[5-(4-{4-[(2S)-2-hydroxy-3-(4-hydroxy-phenoxy)-propylamino]-piperidin-1-yl}-benzylidene)-4-oxo-4,5-dihydro-thiazol-2-yl]-N,N-dimethyl-guanidine;

v) 5-{4-[4-((2S)-2-hydroxy-3-phenoxy-propylamino)-piperidin-1-yl]-benzylidene}-2-morpholin-4-yl-thiazol-4-one;

w) 5-(4-{4-[(2S)-2-hydroxy-3-(4-hydroxy-phenoxy)-propylamino]-piperidin-1-yl}-benzylidene)-2-morpholin-4-yl-thiazol-4-one;

x) 5-(4-{4-[(2S)-2-hydroxy-3-(4-hydroxy-phenoxy)-propylamino]-piperidin-1-yl}-benzylidene)-2-(4-methyl-piperazin-1-yl)-thiazol-4-one;

y) 5-(4-{4-[(2R)-2-(3-chloro-phenyl)-2-hydroxy-ethylamino]-piperidin-1-yl}-benzylidene)-2-morpholin-4-yl-thiazol-4-one;

z) 2-(3-dimethylamino-propylamino)-5-{4-[4-((2S)-2-hydroxy-3-phenoxy -propylamino)-piperidin-1-yl]-benzylidene}-thiazol-4-one;

aa) 2-hexylamino-5-{4-[4-((2S)-2-hydroxy-3-phenoxy-propylamino)-piperidin-1-yl]-benzylidene}-thiazol-4-one;

bb) N-[5-((2R)-2-{1-[4-(2-cyanoamino-4-oxo-4H-thiazol-5-ylidenemethyl)-phenyl]-piperidin-4-ylamino}-1-hydroxy-ethyl)-2-hydroxy-phenyl]-methanesulfonamide;

cc) (2S)-2-[5-(4-{4-[(2S)-2-hydroxy-3-(2-oxo-2,3-dihydro-1H-benzoimidazol-4-yloxy)-propylamino]-piperidin-1-yl}-benzylidene)-4-oxo-4,5-dihydro-thiazol-2-ylamino]-pentanedioic acid;

dd) (2S)-2-[5-(4-{4-[(2R)-2-hydroxy-2-(4-hydroxy-3-methanesulfonylamino-phenyl)-ethylamino]-piperidin-1-yl}-benzylidene)-4-oxo-4,5-dihydro-thiazol-2-ylamino]-pentanedioic acid diethyl ester;

ee) 5-(4-{2-[(2S)-2-hydroxy-3-(4-hydroxy-phenoxy)-propylamino]-ethoxy}-benzylidene)-2-piperidin-1-yl-thiazol-4-one;

ff) 5-{4-[2-((2S)-2-hydroxy-3-phenoxy-propylamino)-ethoxy]-benzylidene}-2-piperidin-1-yl-thiazol-4-one;

gg) N-[2-hydroxy-5-(1-hydroxy-2-{2-[4-(4-oxo-2-piperidin-1-yl-4H-thiazol-5-ylidenemethyl)-phenoxy]-ethylamino}-ethyl)-phenyl]-methanesulfonamide; and hh) 8-hydroxy-5-((2S)-2-hydroxy-3-{2-[4-(4-oxo-2-piperidin-1-yl-4H-thiazol-5-ylidenemethyl)-phenoxy]-ethylamino}-propoxy)-3,4-dihydro-1H-quinolin-2-one or a pharmaceutically acceptable salt thereof.

The compounds of this invention were prepared according to the following schemes from commercially available starting materials or starting materials which can be prepared using literature procedures. These schemes show the preparation of representative compounds of this invention.

According to one route (Scheme 1), 1,4-dioxa-8-azaspiro[4,5]decane is reacted with 4-fluorobenze 1 in the presence of base such as pyridine or potassium carbonate to afford piperidine derivative 2 (Taylor, E. C., Skotnicki, J. S. *Synthesis* 1981, 606). This reaction can be carried out in a polar solvent such as anhydrous acetonitrile, acetone, dimethylformamide, or pyridine. Compound 4 is obtained via a Knoevenagel condensation between an appropriate cyclic lactam 3 and the piperidine derivative 2. In this reaction sodium acetate, β-alanine, glycine, pyridine, piperidine, pyrrolidine, sodium methoxide, potassium acetate, sodium carbonate and the like can be used as a base, and an alcohol such as methanol, ethanol, isopropanol, methoxyethanol and the like, dimethylformamide, water, acetic acid and the like can be used as a solvent.

Arylidene compound 6 can be prepared by one of the following synthetic methods (Unangst, P. C., Connor, D. T., Cetenko, W. A., Sorenson, R. J., Kostlan, C. R., Sircar, J. C., Wright, C. D., Schrier, D. J., Dyer, R. D. *J. Med. Chem.* 1994, 37, 322). One method is a condensation of lactam 4 with amines such as hydroxylamine, N-alkylhydroxyamine, O-alkylhydroxyamine and the like in an alcoholic solvent such as methanol, ethanol, isopropanol and the like at a temperature of 20–100° C. The reaction is conveniently conducted in refluxing methanol or ethanol. Alternatively, alkylation of lactam 4 with iodomethane provides methylmercapto compound 5. Reaction of compound 5 with various amines such as methylamine, 4-(2-aminoethyl)morpholine, piperidine and the like in an alcoholic solvent at a temperature of 20–100° C. gives the desired intermediate 6. The reaction is also conveniently conducted in refluxing methanol or ethanol.

Many amines are commercially available in the hydrochloride salt or sulfate form. Free amines can be easily obtained by methods well known in the art. For example, treatment of N,N-dimethylguanidine sulfate with a stoichiometric equivalent of potassium t-butoxide in ethanol followed by a quick filtration would produce an alcoholic amine solution. Refluxing of methylmercapto compound 5 with the alcoholic amine solution gives the desired intermediate 6.

Ketal hydrolysis is accomplished in the presence of strong acid such as concentrated hydrochloric acid or 10–30% sulfuric acid. The desired final product 9, wherein A, $R_1$, $R_2$, $R_3$, $R_4$, $R_5$, $R_6$, X and Z are as defined above, is prepared by utilizing reductive amination of piperidiones 7 with appropriate arylethanolamines or aryloxypropanolamines 8. The reductive amination can be carried out, for example, with hydrogen and catalytic palladium, or with sodium borohydride, sodium triacetoxyborohydride and the like in a polar solvent such as methanol, dimethylformamide and the like. The final products can be purified by recrystallization, trituration, preparative thin layer chromatography, flash column chromatography on silica gel, or high pressure liquid chromatography. Purification of intermediates can be achieved in the same manner. A salt is optionally produced by the addition of an acid or base, such as hydrogen chloride gas or hydrochloric acid.

According to another route (Scheme 2), the phenol 10 is subjected to an O-alkylation with bromoacetaldehyde diethyl ether via phase-transfer catalysis in the presence of base such as potassium carbonate to give the alkylated compound 11. The phase-transfer catalysts could be used in this reaction includes 18-crown-6, tetrabutylammonium hydrogen sulfate, tetrabutylammonium bromide and the like. The arylidene compound 13 can be prepared, as described in Scheme 1, by substitution of the mercapto compound 12 with amines $R_6H$. In some cases, however, compound 13 could be made directly from the Knoevenagel condensation between intermediate 11, lactams and amines $R_6H$. Ketal hydrolysis followed by reductive amination, as previously described in Scheme 1, furnishes the final product, wherein A, $R_1$, $R_2$, $R_3$, $R_4$, $R_5$, $R_6$, X and Z are as defined above. A salt is optionally produced by the addition of an acid or base, such as hydrogen chloride gas or hydrochloric acid.

Scheme 1
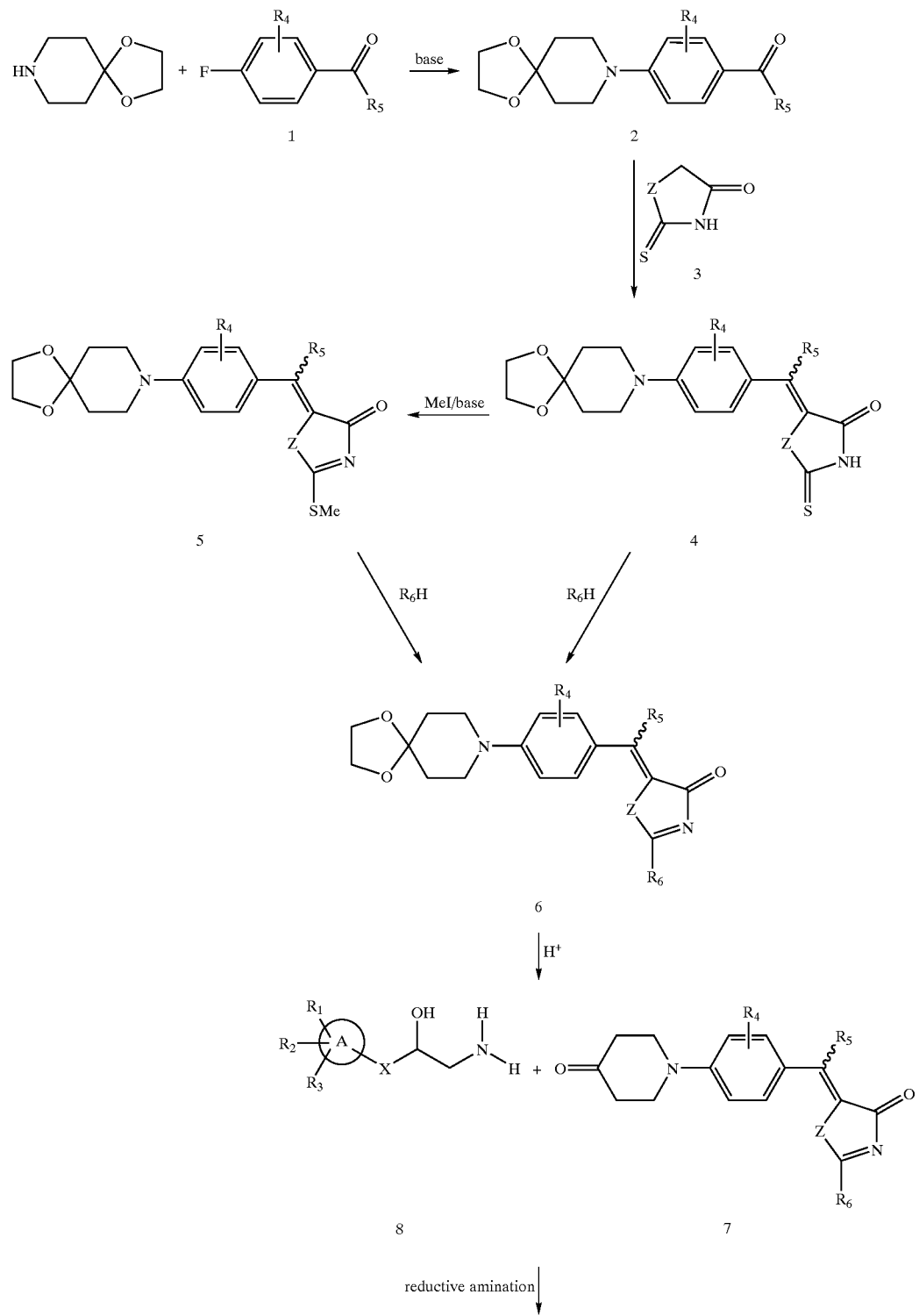

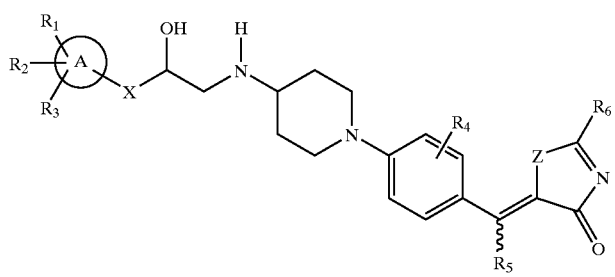
9
Scheme 2
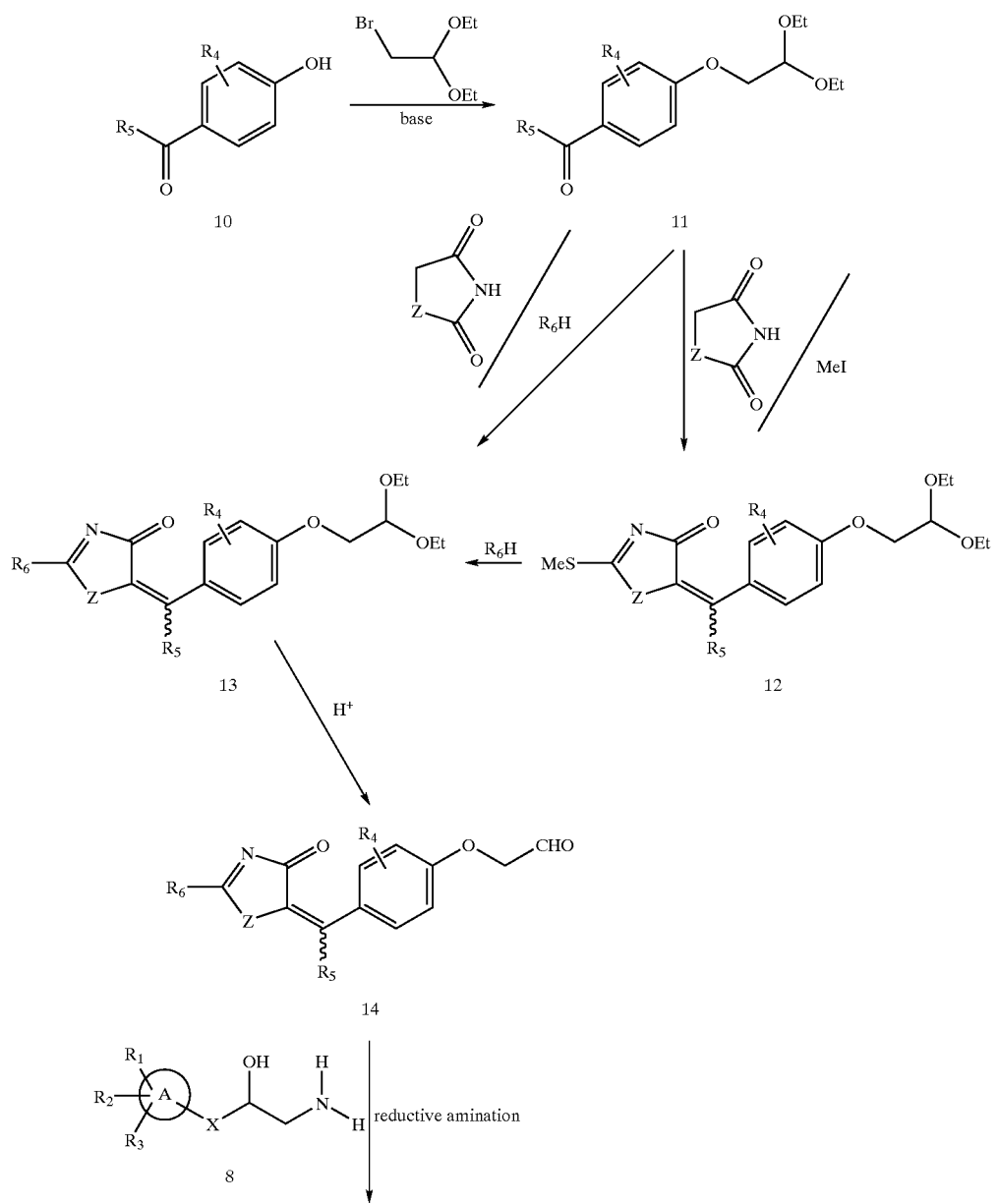

-continued

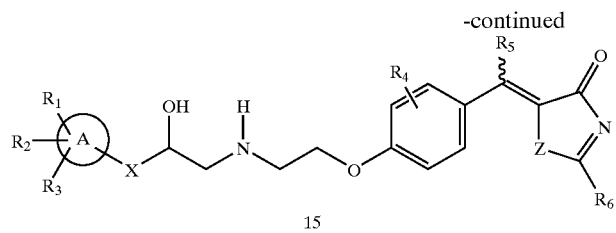

15

Many of arylethanolamines or aryloxypropanolamines 8 are commercially available or readily prepared by known methods [1. Guy, A., Ferroud, D. C., Garreay, R., Godefroy-Falguieres A. *Synthesis*, 1992, 821; 2. Leclerc, G., Bizec, J. C. *J. Med. Chem.*, 1980, 23, 738; 3. Tominaga, M., Ogawa, H., Yo, E., Yamashita, S., Yabuuchi, Y., Nakagawa, K. *Chem. Pharm. Bull.* 1987, 35, 3699]. In one route (Scheme 3) equimolecular amounts of alcohol 16 and enantiomerically pure (2S)-glycidyl 3-nitrobenzene sulfonate 17 are dissolved in an organic solvent such as acetone or dimethylformamide and treated with a base such as sodium hydride or potassium carbonate for 0.5 to 24 hours at a temperature of 20–100° C. to provide oxirane 18. The oxirane 18 is converted to the corresponding amine 20 or 22, wherein A, $R_1$, $R_2$, and $R_3$ are as defined above (provided that in 22 $R_1$, $R_2$, and $R_3$ can not be benzyloxy), by regioselective ring opening of oxirane 18 with either lithium azide in a solvent such as hexamethylphosphoramide followed by reduction with, for example, triphenylphosphine in aqueous tetrahydrofuran, or with one equivalent of dibenzylamine followed by ammonium formate/palladium on carbon reduction. The other enantiomer is available through an analogous preparative sequence with the corresponding (2R)-glycidyl 3-nitrobenzene sulfonate.

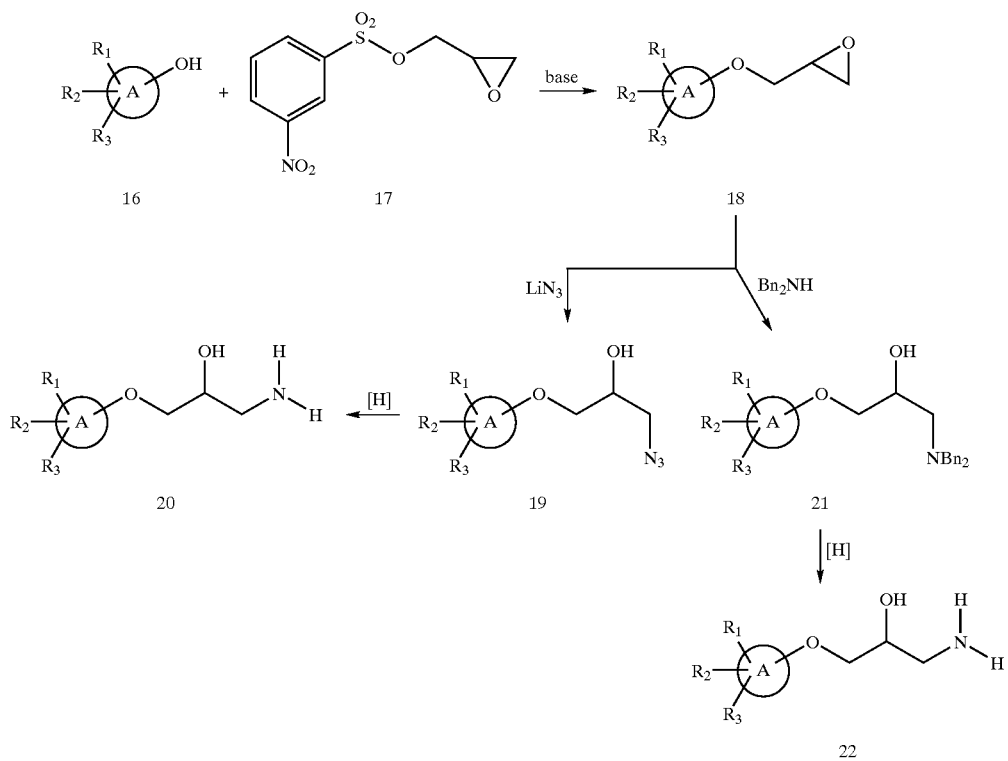

Scheme 3

One route to the desired arylethanolamines 8 is illustrated in Scheme 4. Methylketones 23 are all available commercially or can be prepared by conventional methods disclosed in the art. Compound 23 can be easily converted to the corresponding α-haloketone 24, wherein halo is chlorine, bromine or iodine, using well known halogenation agents such as chlorine, bromine, N-chlorosuccinimide, N-bromosuccinimide and the like. The resultant α-haloketone 24 is then reduced, for example, by sodium borohydride, to give the corresponding racemic alcohol 25. An enantiomerically enriched alcohol 25 may be prepared by asymmetric reduction of α-haloketone 24 with chiral reducing agents such as (+) or (−)-B-chlorodiisopinocampheylborane (DIP-Cl), R or S-Alpine borane, cis-(1R, 2S) or cis (1S, 2R)-oxazaborolidine and the like. The alcohol of intermediate 25 may be protected, for example, as its triethylsilyl ether. In some cases, however, the alcohol protecting group is not required. The halo compound 25 can be easily converted to the corresponding benzylamine 26 by heating to 30–80° C. with a large excess of benzylamine neat or as a solution in a polar solvent such as tetrahydrofuran, acetonitrile or methanol for 1 to 24 hours. The protecting group is then removed, in the case of silyl ether, by treatment of 26 with a fluoride agent such as tetrabutylammonium fluoride. Compound 27 is then subjected to catalytic hydrogenation in the presence of ammonium formate/palladium on carbon to give the desired aminoethanol 28, wherein A, $R_1$, $R_2$ and $R_3$ are as defined above. The reduction is conveniently conducted in refluxing methanol in the presence of a large excess of ammonium formate.

Alternatively, the chloride 25 could be converted to the corresponding amine 28 by treatment with a sodium azide/sodium iodide mixture in a polar solvent such as dimethyl sulfoxide, hexamethylphosphoramide and the like followed by catalytic hydrogenation in the presence of a metal catalyst such as palladium, platinum and the like.

$\beta_2$-adrenergic receptors as described in Tate, K. M.., *Eur. J. Biochem.*, 196:357–361 (1991).

Cloning of Human $\beta_3$-AR Genomic DNA: CDNA was constructed by ligating four polymerase chain reaction (PCR) products using the following primers: an ATG-NarI fragment, sense primer 5'-CTTCCCTACCGCCCC-ACGCGCGATC3', and anti-sense primer 5'CTGGCGC-CCAACGGCCAGTGGCCAGTC3'; a NarI-AccI fragment, 5'TTGGCGCTGATGGCCACTGGCCGTTTG3' as sense and 5'GCGCGTAGACGAAGAGCATCACGAG3' as anti-sense primer; an Accli-StyI fragment, sense primer 5'CTCGTGATGCTCTTCGTCTCACGCGC3' and anti-sense primer 5'GTGAAGGTGCCCATGATGAGAC-CCAAGG3' and a StyI-TAG fragment, with sense primer 5'CCCTGTGCACCTTGGGTCTCATCATGG3' and anti-sense primer 5'CCTCTGCCCCGGTTACCTACCC3'. The corresponding primer sequences are described in *Mantzoros*, Scheme 4

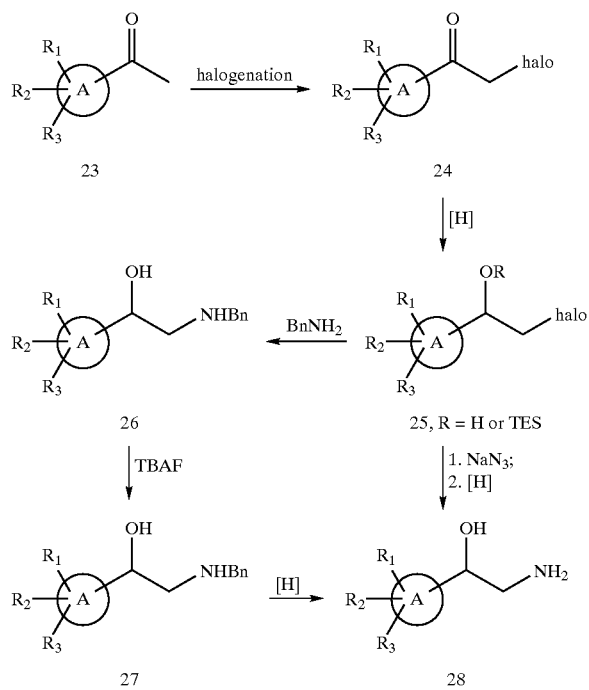

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following standard pharmacological test procedures, which measured the binding selectivity to the $\beta_1$, $\beta_2$, and $\beta_3$ adrenergic receptors. Binding to the receptors was measured in Chinese Hamster ovary (CHO) cells that were transfected with adrenergic receptors. The following briefly summarizes the procedures used and results obtained.

Transfection of CHO cells with $\beta_1$ and $\beta_2$ adrenergic receptors: CHO cells were transfected with human $\beta_1$- or C. S., et.al., *Diabetes* 45: 909–914 (1996). The four fragments are ligated into a pUC 18 plasmid (Gibco-BRL) and sequenced. Full length $\beta_3$ AR clones (402 amino acids) containing the last 6 amino acids of h$\beta_3$-AR are prepared with the $\beta_3$-βARpcDNA3 from ATTC.

Binding Procedure: Clones expressing receptor levels of 70 to 110 fmoles/mg protein were used in the test procedures. CHO cells were grown in 24-well tissue culture plates in Dulbecco's Modified Eagle Media with 10% fetal bovine serum, MEM non-essential amino acids, Penicillin-Streptompycin and Geneticin. On the day of test procedure, growth medium was replaced with preincubation media (Dulbecco's Modified Eagle Media) and incubated for 30 minutes at 37° C. Preincubation medium was replaced with 0.2 ml treatment medium containing DMEM media containing 250 μM IBMX (isobutyl-1-methylxantine) plus 1 mM ascorbic acid with test compound dissolved in DMSO. Test compounds were tested over a concentration range of $10^{-9}$ M to $10^{-5}$ M for $\beta_3$ cells and $10^{-8}$ to $10^{-4}$ M for $\beta_1$ and $\beta_2$ transfected cells. Isoproterenol ($10^{-5}$ M) was used as an internal standard for comparison of activity. Cells were incubated at 37° C. on a rocker for 30 min with the $\beta_3$ cells and 15 min for $\beta_1$ and $\beta_2$ cells. Incubation was stopped with the addition of 0.2N HCl and neutralized with 2.5N NaOH. The plates, containing the cells and neutralized media, were stored at −20 degrees celsius until ready to test for cAMP using the SPA test kit (Amersham).

Data Analysis and Results: Data collected from the SPA test procedure were analyzed as per cent of the maximal isoproterenol response at $10^{-5}$ M. Activity curves were plotted using the SAS statistical and graphics software. $EC_{50}$ values were generated for each compound and the maximal response (IA) developed for each compound is compared to the maximal response of isoproternol at $10^{-5}$ M from the following formula:

$$IA = \frac{\% \text{ activity compound}}{\% \text{ activity isoproterenol}}$$

Table I shows the $\beta_3$-adronergic receptor $EC_{50}$ and IA values for the representative compounds of this invention that were evaluated in this standard pharmacological test procedure. These results show that compounds of the present invention have activity at the $\beta_3$-adrenergic receptor. The compounds of this invention had weaker or no activity at $\beta_1$ and/or $\beta_2$-adrenergic receptor.

TABLE I

| Compound No. | $EC_{50}(\beta_3, nM)$ | $IA(\beta_3)$ |
| --- | --- | --- |
| Example 1 | 9 | 1.0 |
| Example 2 | 22 | 1.0 |
| Example 3 | 30 | 0.52 |
| Example 4 | 230 | 0.6 |
| Example 5 | 9 | 1.22 |
| Example 6 | 10 | 0.94 |
| Example 7 | 9 | 1.06 |
| Example 8 | 8 | 0.75 |
| Example 9 | 7 | 0.81 |
| Example 10 | 19 | 0.69 |
| Example 11 | 8 | 0.83 |
| Example 12 | 9 | 0.95 |
| Example 13 | 3 | 0.86 |
| Example 14 | 1 | 1.0 |
| Example 15 | 6 | 1.1 |
| Example 16 | 75 | 0.96 |
| Example 17 | 2 | 1.0 |
| Example 18 | 3 | 0.89 |
| Example 20 | 937 | 0.79 |
| Example 21 | 400 | 0.93 |
| Example 22 | 40 | 0.58 |
| Example 23 | 76 | 0.78 |
| Example 24 | 1920 | 1.0 |
| Example 25 | 450 | 0.51 |
| Example 26 | 156 | 0.85 |
| Example 27 |  | 0.58 |
| Example 28 | 1 | 1.1 |
| Example 29 | 17 | 0.91 |
| Example 30 | 1 | 1.0 |
| Example 31 | 210 | 0.84 |
| Example 32 | 88 | 0.33 |
| Example 33 | 2 | 0.86 |
| Example 34 | 3 | 1.0 |

Based on the results obtained in these standard pharmacological test procedures, representative compounds of this invention have been shown to be selective $\beta_3$ adrenergic receptor agonists and are therefore useful in treating metabolic disorders related to insulin resistance or hyperglycemia (typically associated with obesity or glucose intolerance), atherosclerosis, gastrointestinal disorders, neurogenetic inflammation, and frequent urination; and are particularly useful in the treatment or inhibition of type II diabetes, and in modulating glucose levels in disorders such as type I diabetes. As used herein, the term modulating means maintaining glucose levels within clinically normal ranges.

As used in accordance with this invention, the term providing an effective amount means either directly administering such a compound of this invention, or administering a prodrug, derivative, or analog which will form an effective amount of the compound of this invention within the body.

It is understood that the effective dosage of the active compounds of this invention may vary depending upon the particular compound utilized, the mode of administration, the condition, and severity thereof, of the condition being treated, as well as the various physical factors related to the individual being treated. As used in accordance with invention, satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg. It is preferred that the administration of one or more of the compounds herein begin at a low dose and be increased until the desired effects are achieved.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, , xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s).

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The compounds of the present invention also possess utility for increasing lean meat deposition and/or improving lean meat to fat ratio in edible animals, i.e. ungulate animals and poultry.

Animal feed compositions effective for increasing lean meat deposition and for improving lean meat to fat ratio in poultry, swine, sheep, goats, and cattle are generally prepared by mixing the compounds of the present invention with a sufficient amount of animal feed to provide from about 1 to 1000 ppm of the compound in the feed. Animal feed supplements can be prepared by admixing about 75% to 95% by weight of a compound of the present invention with about 5% to about 25% by weight of a suitable carrier or diluent. Carriers suitable for use to make up the feed supplement compositions include the following: alfalfa meal, soybean meal, cottonseed oil meal, linseed oil meal, sodium chloride, cornmeal, cane molasses, urea, bone meal, corncob meal and the like. The carrier promotes a uniform distribution of the active ingredients in the finished feed into which the supplement is blended. It thus performs an important function by ensuring proper distribution of the active ingredient throughout the feed. The supplement is used as a top dressing for the feed, it likewise helps to ensure uniformity of distribution of the active material across the top of the dressed feed.

The preferred medicated swine, cattle, sheep and goat feed generally contain from 0.01 to 400 grams of active ingredient per ton of feed, the optimum amount for these animals usually being about 50 to 300 grams per ton of feed. The preferred poultry and domestic pet feed usually contain about 0.01 to 400 grams and preferably 10 to 400 grams of active ingredient per ton of feed.

For parenteral administration the compounds of the present invention may be prepared in the form of a paste or a pellet and administered as an implant, usually under the skin of the head or ear of the animal in which increase in lean meat deposition and improvement in lean mean to fat ratio is sought. In general, parenteral administration involves injection of a sufficient amount of the compounds of the present invention to provide the animal with 0.001 to 100 mg/kg/day of body weight of the active ingredient. The preferred dosage for swine, cattle, sheep and goats is in the range of from 0.001 to 50 mg/kg/day of body weight of active ingredient; whereas, the preferred dose level for poultry and domestic pets is usually in the range of from 0.001 to 35 mg/kg/day of body weight.

Paste formulations can be prepared by dispersing the active compounds in a pharmaceutically acceptable oil such as peanut oil, sesame oil, corn oil or the like. Pellets containing an effective amount of the compounds of the present invention can be prepared by admixing the compounds of the present invention with a diluent such as carbowax, carnuba wax, and the like, and a lubricant, such as magnesium or calcium stearate, can be added to improve the pelleting process. It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body. For the poultry and swine raisers, using the method of the present invention yields leaner animals.

Additionally, the compounds of this invention are useful in increasing the lean mass to fat ratio in domestic pets, for the pet owner or veterinarian who wishes to increase leanness and trim unwanted fat from pet animals, the present invention provides the means by which this can be accomplished.

The following procedures describe the preparation of intermediates useful in the preparation of compounds of this invention.

Intermediate 1

(1R)-2-Amino-1-(3-chloro-phenyl)-ethanol:

Lithium azide (7.5 g, 150 mmol) was added to a solution of (1R)-1-(3-chloro-phenyl)oxirane (15.5 g, 100 mmol) in hexamethylphosphoramide (70 mL). After being stirred at room temperature for 16 hours the suspension was poured into ice-water and the mixture was extracted with diethyl ether. The combined extracts were dried over magnesium sulfate and concentrated. The residue was dissolved in 550 mL of tetrahydrofuran/water (10:1) and triphenylphosphine (30 g, 114 mmol) was added. After overnight stirring at room temperature, the solvents were removed and the residue was purified by column chromatography on silica gel using triethylamine-methanol-methylene chloride (1:1:8) as the eluent to give the title compound as a free base.

The title compound was characterized as its hydrochloric salt: The free base from above was then dissolved in diethyl ether and slowly treated with hydrogen chloride gas. The precipitate was collected by filtration to yield 15 g (72%) of the title compound as a white powder; $^1$H NMR (300 MHz, DMSO-$d_6$) δ 2.83 (dd, J=12.8, 9.5 Hz, 1 H), 3.06 (dd, J=12.8, 3.2 Hz, 1 H), 4.80–4.90 (m, 1 H), 6.22 (d, J=4.0 Hz, 1 H), 7.10–7.75 (m, 4 H), 8.08 (brs, 2 H ); MS (ES) m/z: 171.7, 173.7 (MH$^+$); HRMS Calcd. for $C_8H_{10}ClNO(MH^+)$: 172.0529. Found: 172.0531.

Intermediate 2

(2S)-2-Phenoxymethyl-oxirane:

A solution of phenol (9.4 g, 100 mmol) and (2S)-(+) glycidyl 3-nitrobenzesulfonate(25.9 g, 100 mmol) in 500 mL of acetone was treated with 3 equivalents of potassium carbonate (41.5 g, 300 mmol) and stirred at reflux for 1 day. The suspension was cooled to ambient temperature; the solid was filtered; and the filtrate concentrated to dryness. The residue was partitioned between methylene chloride and water and the aqueous layer was extracted with methylene chloride. The organic layers were combined and dried over magnesium sulfate and concentrated to give the title compound (15.0 g, 99%) as an orange oil; $^1$H NMR (300 MHz, CDCl$_3$) δ 6 2.76 (dd, J=4.9, 2.6 Hz, 1 H), 2.90 (dd, J=4.9, 4.9 Hz, 1 H), 3.30–3.40 (m, 1 H), 3.95 (dd, J=11.0, 5.4 Hz, 1 H), 4.18 (dd, J=11.0, 3.0 Hz, 1 H), 6.85–7.00 (m, 3 H), 7.25–7.35 (m, 2 H); MS (ES) m/z: 151.0 (MH$^+$).

Intermediate 3

(2S)-1-Amino-3-phenoxypropan-2-ol:

The title compound was prepared from (2S)-2-phenoxymethyl-oxirane (which was obtained in Intermediate 2) according to the procedure of Intermediate 1 as a white solid; $^1$H NMR (300 MHz, DMSO-d$_6$) δ 2.56 (dd, J=12.8, 6.3 Hz, 1 H), 2.67 (dd, J=12.8, 4.9 Hz, 1 H), 3.65–3.75 (m, 1 H), 3.82 (dd, J=9.8, 6.0 Hz, 1 H), 3.93 (dd, J=9.8, 5.0 Hz, 1 H), 6.85–6.95 (m, 3 H), 7.20–7.30 (m, 2 H); MS (ES) m/z: 167.7 (MH$^+$); HRMS Calcd. for C$_9$H$_{13}$NO$_2$ (M$^+$): 167.0946. Found: 167.0945.

Intermediate 4

(2S)-1-Amino-3-(4-benzyloxy-phenoxy)-propan-2-ol:

The title compound was prepared from (2S)-2-(4-benzyloxy-phenoxymethyl-oxirane (Sher, P. M., et al., EP 0 714 883) according to the procedure of Intermediate 1 as a white solid; $^1$H NMR (300 MHz, CDCl$_3$) δ 2.50–2.70 (m, 2 H), 3.33 (brs, 2 H), 3.60–3.90 (m, 3 H), 5.02 (s, 2 H), 6.90 (d, J=6.7 Hz, 2 H), 6.93 (d,J=6.7 Hz, 2 H), 7.25–7.50 (m, 5 H); MS (ES) m/z: 274.1 (MH$^+$); HRMS Calcd. for C$_{16}$H$_{19}$NO$_3$(M$^+$): 273.1365. Found: 273.1347. Anal. Calcd. for C$_{16}$H$_{19}$NO$_3$: C, 70.31; H, 7.01; N, 5.12. Found: C, 70.39; H, 6.80; N, 5.23.

Intermediate 5

(2S)-1-Amino-3-(4-hydroxy-phenoxy)-propan-2-ol:

A mixture of (2S)-1-amino-3-(4-benzyloxy-phenoxy)-propan-2-ol (which was obtained in Intermediate 4) (0.9 g, 3.3 mmol), 0.2 mL of acetic acid and 10% palladium on carbon (0.3 g) in 70 mL of ethanol was pressurized with 20 psi hydrogen and shaken over 2 hours. The catalyst was then removed by filtering through a short pad of silica gel and the solvent was removed to give the title compound as an off-white solid; $^1$H NMR (300 MHz, DMSO-d$_6$) δ 1.86 (s, 1 H), 2.66 (dd, J=12.8, 5.3 Hz, 1H), 2.85 (dd, J=12.8, 3.5 Hz, 1H), 3.79–3.95 (m, 3 H), 6.67 (d, J=6.6 Hz, 2H), 6.75 (d, J=6.6 Hz, 2 H); MS (ES) m/z: 183.1 (MH$^+$); HRMS Calcd. for C$_9$H$_{13}$NO$_3$(MH$^+$): 183.0895. Found: 183.0892.

Intermediate 6

N-[2-Benzyloxy-5-(2-dibenzylamino-1-oxo-ethyl)-phenyl]-methanesulfonamide:

N-[2-Benzyloxy-5-(2-chloro-1-oxo-ethyl)-phenyl]-methanesulfonamide (Washburn, W. N., et al., EP 0 659 737) (17.0 g, 42.8 mmol) was dissolved in 200 mL of dimethylformamide and treated with dibenzylamine (22.0 g, 110 mmol). The mixture was stirred at room temperature overnight and then the solvent was removed. The residue was purified by silica gel chromatography using 20–50% ethyl acetate/hexanes as eluent to give the title compound as a white solid; $^1$H NMR (300 MHz, CDCl$_3$) δ 2.94 (s, 3 H), 3.77 (s, 2 H), 3.82 (s, 2 H), 5.16 (s, 2 H), 6.75 (brs, 1 H), 6.96 (d, J=8.7 Hz, 1 H), 7.20–7.50 (m, 15 H), 7.67 (dd, J=8.7, 2.1 Hz, 1 H), 8.10 (d, J=2.1 Hz, 1 H); MS (ES) m/z: 515.2 (MH$^+$); HRMS Calcd. for C$_{30}$H$_{30}$N$_2$O$_4$S(M$^{30}$)$^:$ 514.1926. Found: 514.1927.

Intermediate 7

N-[2-Benzyloxy-5-(2-dibenzylamino-1-hydroxy-ethyl)-phenyl]-methanesulfonamide:

Sodium borohydride (0.37 g, 9.7 mmol) was added in portions to a stirred solution of N-[2-benzyloxy-5-(2-dibenzylamino-1-oxo-ethyl)-phenyl]-methanesulfonamide (which was obtained in Intermediate 6) (1.0 g, 1.9 mmol) in 20 mL of methanol/tetrahydrofuran (5:2) at room temperature and the resulting solution was stirred for 2 hours. Methylene chloride was added and the resulting solution was washed with aqueous sodium bicarbonate, dried over magnesium sulfate and the solvents were removed. Recrystallization from methylene chloride/hexanes gave the title compound as a crystalline solid; $^1$H NMR (300 MHz, CDCl$_3$) δ 2.58 (d, J=6.7 Hz, 2 H), 2.86 (s, 2 H), 2.92 (s, 2 H), 3.55 (d, J=13.5 Hz, 2 H), 3.70 (d, J=13.5 Hz, 2 H), 4.11 (s, 1 H), 4.64 (t, J=6.7 Hz, 1 H), 5.10 (s, 2 H), 6.92 (d, J=8.5 Hz, 1 H), 7.00 (dd, J=8.5, 2.0 Hz, 1 H), 7.20–7.50 (m, 16 H), 7.89 (brs, 1 H); MS (ES) m/z: 517.1 (MH$^+$); HRMS Calcd. for C$_{30}$H$_{32}$N$_2$O$_4$S(M$^+$): 516.2083. Found: 516.2074.

Intermediate 8

N-[5-((1R)-2-Azido-1-hydroxy-ethyl)-2-benzyloxy-phenyl]-methanesulfonamide:

To a stirred solution of N-[2-benzyloxy-5-(2-bromo-1-hydroxy-ethyl)-phenyl]-methanesulfonamide (Washburn, W. N., et al., EP 0 659 737) (15.05 g, 38 mmol) in dimethyl sulfoxide (150 ml) was added sodium iodide (3.76 g, 376 mmol) and sodium azide (9.48 g, 150 mmol). The mixture was stirred for 5 days under nitrogen atmosphere. The reaction mixture was poured onto water and extracted three times with ethyl acetate. The combined organic layers were dried over sodium sulfate and concentrated. The residue was triturated with water and hexanes to give the title compound as a yellow solid (12.85 g, 94%): $^1$H NMR (300 MHz, CDCl$_3$) δ 2.93(s, 3 H), 3.47(d, J=5.4 Hz, 2 H), 4.84(t, J=5.4 Hz, 1 H), 5.11(s, 2 H), 6.80(s, 1 H), 6.99(d, J=8.4 Hz, 1 H), 7.15(dd, J=8.4 Hz, 2.1 Hz, 1H), 7.26(s, 1 H), 7.30–5.50(m, 5 H), 7.53(d, J=2.1 Hz, 1 H); MS (ES) m/z 361.4 ((M-H)-, 70%).

Intermediate 9

N-[5-(2-Amino-1-hydroxy-ethyl)-2-hydroxy-phenyl]-methanesulfonamide:

To a stirred suspension of N-[2-benzyloxy-5-(2-dibenzylamino-1-hydroxy-ethyl)-phenyl]-methanesulfonamide (which was obtained in Intermediate 7)(1.03g, 2 mmol) and 10% palladium on carbon (0.4 g) in methanol (100 mL) at room temperature was added anhydrous ammonium formate (1.26 g, 20 mmol) under a nitrogen atmosphere. The resulting mixture was refluxed for 2 hours. After cooling to room temperature the catalyst was removed by filtration through a celite pad and washed with methanol. The filtrate was evaporated under reduced pressure to give the titled compound (Leclerc, G., Bizec, J. C. J. Med. Chem., 1980, 23, 738) as a pale yellowish solid; $^1$H NMR (300 MHz, DMSO-d$_6$) δ 2.62 (dd, J=12.6, 8.7 Hz, 1 H), 2.75 (dd, J=12.6, 3.7 Hz, 1 H), 2.90 (s, 3 H), 4.47 (dd, J=8.7, 3.7 Hz, 1 H), 6.84 (d, J=9.1 Hz, 1 H), 6.96 (dd, J=9.1, 2.0 Hz, 1 H), 7.16 (d, J=2.1 Hz, 1 H), 8.44 (s, 1 H); MS (ES) m/z: 246.7 (MH$^+$); HRMS Calcd. for C$_9$H$_{14}$N$_2$O$_4$S(M$^+$): 246.0674. Found: 246.0672.

Intermediate 10

N-[5-(2-Amino-(1R)-1-hydroxy-ethyl)-2-hydroxy-phenyl]-methanesulfonamide:

Method A: A mixture of N-{2-benzyloxy-5-(2-iodo-(1R)-1-[(triethylsilyl)oxy]-ethyl)-phenyl}-methanesulfonamide (Washburn, W. N., et al., EP 0 659 737) (8.60 g, 15.3 mmol) and benzylamine (21.4 g, 200 mmol) was heated at 60° C. for 24 hours. The reaction mixture was cooled, diluted with hexanes (500 mL), and the residue was washed with diethyl ether. The combined solvents were removed and the residue was purified by silica gel column eluting with 30 to 100% diethyl ether/hexanes. The fractions with molecular weight of 540 were concentrated and re-dissolved in 200 mL of tetrahydrofuran and tetrabutylammonium fluoride (20 mL, 1.0 M solution in tetrahydrofuran) was added. After stirring at room temperature for 4 hours the reaction mixture was then poured into water and extracted with methylene chloride. The organic layers were passed through a short pad of silica gel eluting with 10% methanol/methylene chloride. The solvents were removed and the residue was dissolved in methanol (200 mL). 10% Palladium on carbon (0.6 g) and anhydrous ammonium formate (6.3 g, 100 mmol) were added. The resulting mixture was refluxed under a nitrogen atmosphere for 2 hours. After cooling to room temperature the catalyst was removed by filtration through a celite pad and washed with methanol. The filtrate was evaporated under reduced pressure to give the title compound as an off-white solid; $^1$H NMR (300 MHz, MeOH-d$^4$) δ 2.95 (s, 3 H), 2.99 (dd, J=9.7, 9.2 Hz, 1 H), 3.07 (dd, J=9.7, 3.6 Hz, 1 H), 4.75 (dd, J=9.2, 3.6 Hz, 1 H), 6.90 (d, J=8.3 Hz, 1 H), 7.12 (dd, J=8.3, 2.1 Hz, 1 H), 7.38 (d, J=2.1 Hz, 1 H), 8.44 (s, 1 H); MS (ES) m/z: 246.7 (MH$^+$); HRMS Calcd. for $C_9H_{14}N_2O_4S(M^+)$: 246.0674. Found: 246.0672. Method B: A mixture of N-[5-((1R)-2-azido-1-hydroxy-ethyl)-2-benzyloxy-phenyl]-methanesulfonamide (which was obtained in Intermediate 8)(12.85 g, 0.037 mol) and 10% palladium on carbon (2.75 g) in ethanol (100 ml) was hydrogenated under 45 psi for two days. The reaction mixture was filtered through celite and concentrated. The title compound was recovered as an off-white solid (6.08 g, 66%).

Intermediate 11
8-Benzyloxy-(5S)-5-oxiranylmethoxy-3,4-dihydro-1H-quinolin-2-one:

The title compound was prepared from 8-benzyloxy-5-hydroxy-3,4-dihydro-1H-quinolin-2-one (Tominaga, M., Ogawa, H., Yo, E., Yamashita, S., Yabuuchi, Y., Nakagawa, K. *Chem. Pharm. Bull.* 1987, 35, 3699) according to the procedure of Intermediate 2; $^1$H NMR (300 MHz, DMSO-d$_6$) δ 2.41 (t, J=7.1 Hz, 2 H), 2.69 (dd, J=5.1, 2.7 Hz, 1 H), 2.75–2.86 (m, 4 H), 3.78 (dd, J=11.4, 6.3 Hz, 1 H), 4.23 (dd, J=11.4, 2.6 Hz, 1 H), 5.09 (s, 2 H), 6.54 (d, J=9.0 Hz, 2 H), 6.86 (d, J=9.0 Hz, 2 H), 7.25–7.45 (m, 3 H), 7.51 (d, J=8.2 Hz, 2 H), 9.08 (s, 1 H); MS (ES) m/z: 326.0 (MH$^+$); HRMS Calcd. for $C_{19}H_{20}NO_4(MH^+)$: 326.1392. Found: 326.1343. Anal. Calcd. for $C_{19}H_{19}NO_4$: C, 70.14; H, 5.89; N, 4.30. Found: C, 70.14; H, 5.69; N, 4.20.

Intermediate 12
5-(3-Amino-(2S)-2-hydroxy-propoxy)-8-hydroxy-3,4-dihydro-1 H-quinolin-2-one:

Dibenzylamine (1.46g, 7.4 mmol) was added to a stirred solution of 8-benzyloxy-(5S)-5-oxiranylmethoxy-3,4-dihydro-1H-quinolin-2-one(which was obtained in Intermediate 11) (2.0 g, 6.2 mmol) in 100 mL of methanol. After refluxing overnight the mixture was cooled down to room temperature and 10% palladium on carbon (0.5 g) and ammonium formate (3.15 g, 50 mmol) were added. The suspension was refluxed for another hour. After cooling the suspension the reaction mixture was filtered through celite. The filtrate was concentrated to give the title compound as a pale grey solid; $^1$H NMR (300 MHz, DMSO-d$_6$) δ 2.42(t, J=7.1 Hz, 2 H), 2.74 (dd, J=12.8, 8.2 Hz, 1 H), 2.81 (t, J=7.0 Hz, 2 H), 2.95 (dd, J=12.8, 3.4 Hz, 1 H), 3.65–3.95 (m, 3 H), 6.45 (d, J=8.8 Hz, 2 H), 6.62 (d, J=8.8 Hz, 2 H), 8.38 (s, 1 H), 8.77 (brs, 1 H); MS (ES) m/z: 252.9 (MH$^+$); HRMS Calcd. for $C_{12}H_{16}N_2O_4(M^+)$: 252.1188. Found: 252.1199.

Intermediate 13
N-Benzyl-N-(2-benzyloxy-5-oxiranylmethoxy-phenyl)-methanesulfonamide:

The title compound was prepared from N-benzyl-N-(2-benzoxy-5-hydro-phenyl)-methanesulfonamide(Kaiser, C.; Jen, T.; Garvey, E.; and Bowen, W. D. *J. Med. Chem.* 1977, 20, 687) according to the procedure of Intermediate 2 as a white solid; $^1$H NMR (300 MHz, DMSO-d$_6$) δ 2.63(dd, J=5.1, 2.6 Hz, 1 H), 2.80(t, J=4.9 Hz, 1 H), 3.10–3.20(m, 1 H), 3.66(dd, J=11.4, 6.6 Hz, 1 H), 4.16(dd, J=11.4, 2.6 Hz, 1 H), 4.73(brs, 2 H), 5.12(s, 2 H), 6.69 (d, J=3.1 Hz, 1 H), 6.88(dd, J=9.1, 3.1 Hz, 1 H), 7.08 (d, J=9.1 Hz, 1 H), 7.15–7.60(m, 10 H); MS (ES) m/z:439.9 (MH$^+$, 100%); HRMS Calcd. for $C_{24}H_{25}NO_5S$ (M+): 439.1454. Found: 439.1457.

Intermediate 14
N-[5-((2S)-3-Amino-2-hydroxy-propoxy)-2-hydroxy-phenyl]-methanesulfonamide:

The title compound was prepared from N-benzyl-N-(2-benzyloxy-5-oxiranylmethoxy-phenyl)-methanesulfonamide(which was obtained in Intermediate 13) according to the procedure of Intermediate 12 as a pale grey solid; $^1$H NMR (300 MHz, DMSO-d$_6$) δ 2.61(dd, J=12.7, 6.1 Hz, 1 H), 2.75(dd, J=12.7, 3.5 Hz, 1 H), 2.86(s, 3 H), 3.69–3.90(m, 3 H), 6.55(dd, J=8.7, 3.1 Hz, 1 H), 6.70(d, J=8.7 H), 6.75 (d, J=3.1 Hz, 1 H); MS (ES) m/z: 276.8 (MH$^+$, 100%); HRMS Calcd. for $C_{10}H_{16}N_2O_5S$ (M+): 276.0780. Found: 276.0792.

Intermediate 15
5-[4(1,4-Dioxa-8-aza-spiro[4,5]dec-8-yl)-benzylidene]-2-thioxothiazolidin-4-one:

A mixture of 4-(1,4-dioxa-8-aza-spiro[4,5]dec-8-yl)-benzaldehyde (Taylor, E. C., Skotnicki, J. S. *Synthesis*, 1981, 606) (4.96 g, 20 mol), rhodanine (2.66 g, 20 mmol), and β-alanine (2.0 g, 22.5 mmol) in 50 mL of acetic acid was refluxed for 2 hours. The solid which was formed on cooling the solution was collected to give the title compound as a red solid (4.8 g, 66%); $^1$H NMR (300 MHz, CDCl$_3$) δ 1.81 (t, J=5.5 Hz, 4 H), 3.55 (t, J=5.5 Hz, 4 H), 4.00 (s, 4 H), 6.92 (d, J=8.9 Hz, 2 H), 7.58 (d, J=8.9 Hz, 2 H), 7.38 (s, 1 H); MS (ES) m/z: 362.8 (MH$^+$); HRMS Calcd. for $C_{17}H_{19}N_2O_3S_2$ (MH$^+$): 363.0837. Found: 363.0852. Anal. Calcd. for $C_{17}H_{18}N_2O_3S_2$: C, 56.33; H, 5.01; N, 7.73. Found: C, 56.28; H, 4.89; N, 7.73.

Intermediate 16
5-[4-(1,4-Dioxa-8-aza-spiro[4,5]dec-8-yl)-benzylidene]-2-methylsulfanyl-thiazo-4-one:

A mixture of 5-[4(1,4-dioxa-8-aza-spiro[4,5]dec-6-yl)-benzylidene]-2-thioxothiazolidin-4-one(which was obtained in Intermediate 15) (1.50 g, 4.14 mmol), N,N-diisopropylethylamine (0.65 g, 5 mmol), iodomethane (1.13 g, 8 mmol) in ethanol (50 mL) was stirred at room temperature overnight. Water (300 mL) was then added and the mixture was stirred for another hour. The solid which was formed was collected and dried to give the title compound as a red solid; $^1$H NMR (300 MHz, CDCl$_3$) δ 1.80 (t, J=5.8 Hz, 4 H), 2.88 (s, 3 H), 3.50 (t, J=5.8 Hz, 4 H), 4.00 (s, 4 H), 6.90 (d, J=9.0 Hz, 2 H), 7.45 (d, J=9.0 Hz, 2 H), 7.80 (s, 1 H); MS (ES) m/z: 376.9 (MH$^+$, 100%), 752.9 ((2M+H)$^+$, 5%); HRMS Calcd. for $C_{18}H_{20}N_2O_3S_2$ (M$^{+)}$: 376.0915. Found: 376.0888. Anal. Calcd. for $C_{18}H_{20}N^2O_3S_2$: C, 57.42; H, 5.35; N, 7.44. Found: C, 57.34; H, 5.18; N, 7.34.

Intermediate 17

5-[4-(1,4-Dioxa-8-aza-spiro[4,5]dec-8-yl)-benzylidene]-2-methylamino-thiazo-4-one:

A mixture of 5-[4-(1,4-dioxa-8-aza-spiro[4,5]dec-8-yl)-benzylidene]-2-methylsulfanyl-thiazo-4-one(which was obtained in Intermediate 16) (0.56 g, 1.5 mmol) and methylamine (7.5 mL, 2.0 M solution in tetrahydrofuran) in ethanol (100 mL) was refluxed overnight. After cooling to room temperature hexanes (70 mL) was added and the solid which was formed was collected to give the title compound as a yellowish solid (olefinic cis/trans mixture, ratio 3 to 1); $^1$H NMR (300 MHz, CDCl$_3$) δ 1.75–1.85 (m, 4 H), 3.19 (s, 3 H), 3.40–3.50 (m, 4 H), 4.00(s, 4 H), 6.98 (d, J=9.0 Hz, 2 H), 7.46 (d, J=9.0 Hz, 2 H), 7.71 (s, 1 H); MS (ES) m/z: 359.9 (MH$^+$, 100%), 719.0 ((2M+H)$^+$, 10%); HRMS Calcd. for $C_{18}H_{21}N_3O_3S$ (M$^+$): 359.1304. Found: 359.1307.

Intermediate 18

1-[4-(2-Methylamino-4-oxo-4H-thiazol-5-ylidenemethyl)-phenyl]-piperdin-4-one:

5-[4-(1,4-Dioxa-8-aza-spiro[4,5]dec-8-yl)-benzylidene]-2-methylamino-thiazo-4-one(which was obtained in Intermediate 17) (0.25 g, 0.7 mmol) was treated with concentrated hydrochloric acid (18 mL) at room temperature. After 30 minutes the solution was neutralized with ~28% ammonium hydroxide and the precipitate was collected by filtration, and dried to give the title compound as a yellowish solid (0.20g, 91%, olefinic cis/trans mixture, ratio 5 to 1); $^1$H NMR (300 MHz, DMSO-d$_6$) δ 2.43 (t, J=5.9Hz, 4 H), 3.05 (s, 3 H), 3.73 (t, J=5.9Hz, 4 H), 7.13 (d, J=7.3 Hz, 2 H), 7.46 (d, J=7.3 Hz, 2 H), 7.50 (s, 1 H), 9.41 (brs, 1 H); MS (ES) m/z: 315.8 (MH$^+$, 100%), 631.0 ((2M+H)$^+$, 10%); HRMS Calcd. for $C_{16}H_{17}N_3O_2S$ (M$^+$): 315.1041. Found: 315.1057.

Intermediate 19

5-[4-(1,4-Dioxa-8-aza-spiro[4,5]dec-8-yl)-benzylidene]-2-(2-morpholin-4-yl -ethylamino)-thiazo-4-one:

The title compound was prepared from 5-[4-(1,4-dioxa-8-aza-spiro[4,5]dec-8-yl)-benzylidene]-2-methylsulfanyl-thiazo-4-one(which was obtained in Intermediate 16) and 4-(2-aminoethyl) morpholine according to the procedure of Intermediate 17 as a yellowish solid (one major isomer); $^1$H NMR (300 MHz, DMSO-d$_6$) δ 1.68 (t, J=5.5 Hz, 4 H), 2.35–2.55 (m, 6 H), 3.44 (t, J=5.5 Hz, 4 H), 3.55–3.65 (m, 6 H), 3.92(s, 4 H), 7.07 (d, J=8.9 Hz, 2 H), 7.40 (d, J=8.9 Hz, 2 H), 7.47 (s, 1 H), 9.43 (brs, 1 H); MS (ES) m/z: 229.9 ((M+2H)$^{2+}$, 40%), 458.9 (MH$^+$, 100%), 917.2 ((2M+H)$^+$, 3%); HRMS Calcd. for $C_{23}H_{30}N_4O_4S$ (M$^+$): 458.1988. Found: 458.1979.

Intermediate 20

1-{4-[2-(2-Morpholin-4-yl-ethylamino)-4-oxo-4H-thiazol-5-ylidenemethyl]-phenyl}-piperidin-4-one:

The title compound was prepared from 5-[4-(1,4-dioxa-8-aza-spiro[4,5]dec-8-yl-benzylidene]-2-(2-morpholin-4-yl-ethylamino)-thiazo-4-one(which was obtained in Intermediate 19) according to the procedure of Intermediate 18 as a yellowish solid (one major isomer); $^1$H NMR (300 MHz, DMSO-d$_6$) δ 2.30–2.55(m, 10 H), 3.50–3.70 (m, 6 H), 3.74 (t, J=5.9 Hz, 4 H), 7.11 (d, J=8.7 Hz, 2 H), 7.45 (d, J=8.7 Hz, 2 H), 7.50 (s, 1 H), 9.46 (brs, 1 H); MS (ES) m/z: 414.9 (MH$^+$, 100%), 829.1 ((2M+H)$^+$, 2%); HRMS Calcd. for $C_{21}H_{26}N_4O_3S$ (M$^+$): 414.1726. Found: 414.1734.

Intermediate 21

1-{4-[2-(1-Benzyl-piperidn-4-ylamino)-4-oxo-4H-thiazol-5-ylidenemethyl]-phenyl}-piperidin-4-one:

The title compound was prepared from 5-[4-(1,4-dioxa-8-aza-spiro[4,5]dec-8-yl)-benzylidene]-2-methylsulfanyl-thiazo-4-one(which was obtained in Intermediate 16) and 4-amino-1-benzylpiperidine according to the procedures of Intermediate 17 and Intermediate 18 as a yellowish solid (one major isomer); $^1$H NMR (300 MHz, DMSO-d$_6$) δ 1.50–4.00(m, 9 H), 2.43 (t, J=5.9 Hz, 4 H), 3.33 (s, 2 H),3.74 (t, J=5.9 Hz, 4 H), 7.12 (d, J=8.7 Hz, 2 H), 7.20–7.50 (m, 5 H), 7.44 (d, J=8.7 Hz, 2 H), 7.52 (s, 1 H); MS (ES) m/z: 475.0 (MH$^+$, 100%), 949.3 ((2M+H)$^+$, 2%); HRMS Calcd. for $C_{27}H_{30}N_4O_2S$ (M$^+$): 474.2089. Found: 474.2085.

Intermediate 22

3-[5-(4-Oxo-piperidin-1-yl)-benzylidene-4-oxo-4,5-dihydrothiazol-2-ylamino]-propionic acid ethyl ester The title compound was prepared from 5-[4-(1,4-dioxa-8-aza-spiro[4,5]dec-8-yl)-benzylidene]-2-methylsulfanyl-thiazo-4-one(which was obtained in Intermediate 16) and β-alanine ethyl ester according to the procedures of Intermediate 17 and Intermediate 18 as a yellowish solid (one major isomer); MS (ES) m/z: 402.2 (MH$^+$, 100%).

Intermediate 23

N,N-Dimethyl-N'-{4-oxo-5-[4-(4-oxo-piperidin-1-yl)-benzylidene]-4,5-dihydro-thiazol-2-yl}-guanidine:

The title compound was prepared from 5-[4-(1,4-dioxa-8-aza-spiro[4,5]dec-8-yl)benzylidene]-2-methylsulfanyl-thiazo-4-one(which was obtained in Intermediate 16) and 1,1-dimethylguanidine sulfate according to the procedures of Intermediate 17 and Intermediate 18 as a yellowish solid (one major isomer); $^1$H NMR (300 MHz, DMSO-d$_6$) δ 2.49 (t, J=6.0 Hz, 4 H), 2.90–3.20 (m, 6 H), 3.73 (t, J=6.0 Hz, 4 H), 7.10 (d, J=9.0 Hz, 2 H), 7.47 (d, J=9.0 Hz, 2 H), 7.50 (s, 1 H); MS (ES) m/z: 372.0 (MH$^+$); HRMS Calcd. for $C_{18}H_{22}N_5O_2S$ (MH$^+$): 372.1416. Found: 372.1404.

Intermediate 24

5-[4-(1,4-Dioxa-8-aza-spiro[4,5]dec-8-yl)benzylidene]-2-hydroxyamino-thiazol-4-one:

A solution of hydroxyamine hydrochloride (2.09 g, 30 mmol) in methanol (50 mL) was treated in portions with potassium tert-butoxide (3.25 g, 29 mmol). The mixture was stirred for 30 minutes and then rapidly filtered into a suspension of 5-[4(1,4-dioxa-8-aza-spiro[4,5]dec-6-yl)-benzylidene]-2-thioxothiazolidin-4-one (which was obtained in Intermediate 15)(1.81 g, 5 mmol) in methanol (200 mL). The reaction mixture was refluxed overnight. Upon cooling the precipitated solid was collected to give the title compound as a yellowish solid (one major isomer); $^1$H NMR (300 MHz, DMSO-d$_6$) δ 1.68 (t, J=5.5 Hz, 4 H), 3.16 (d, J=5.2 Hz, 1 H), 3.44 (t, J=5.5 Hz, 4 H), 3.92 (s, 4 H), 7.07 (d, J=8.7 Hz, 2 H), 7.40 (d, J=8.7 Hz, 2 H), 7.45 (s, 1 H); MS (ES) m/z: 361.8 (MH$^+$); HRMS Calcd. for $C_{17}H_{19}N_3O_4S$ (M$^+$): 361.1096. Found: 361.1113.

Intermediate 25

1-[4-(4-Oxo-2-piperidin-1-yl-4H-thiazol-5-ylidenemethyl)-phenyl]-piperidin-4-one:

The title compound was prepared from 5-[4-(1,4-dioxa-8-aza-spiro[4,5]dec-8-yl)-benzylidene]-2-methylsulfanyl-thiazo-4-one(which was obtained in Intermediate 16) and piperidine according to the procedures of Intermediate 17 and Intermediate 18 as a yellowish solid (one major isomer); $^1$H NMR (300 MHz, DMSO-d$_6$) δ 1.50–1.75(m, 6 H), 2.43 (t, J=5.9 Hz, 4 H), 3.55–3.70 (m, 2 H), 3.74 (t, J=5.9 Hz, 4

H), 3.80–3.95 (m, 2 H), 7.10 (d, J=8.9 Hz, 2 H), 7.51 (d, J=8.9 Hz, 2 H), 7.54 (s, 1 H); MS (ES) m/z: 370.0 (MH$^+$, 100%), 739.1 ((2M+H)$^+$, 5%); HRMS Calcd. for $C_{20}H_{23}N_3O_2S$ (M$^+$): 369.1511. Found: 369.1518.

Intermediate 26

5-[4-(1,4-Dioxa-8-aza-spiro[4.5]dec-8-yl)-benzylidene]-2-morpholin-4-yl-thiazol-4-one:

The title compound was prepared from 5-[4-(1,4-dioxa-8-aza-spiro[4,5]dec-8-yl)benzylidene]-2-methylsulfanyl-thiazo-4-one(which was obtained in Intermediate 16) and morpholine according to the procedure of Intermediate 17 as a yellowish solid (one major isomer); $^1$H NMR (300 MHz, DMSO-d$_6$) δ 1.68 (brt, J=5.6 Hz, 4 H), 3.45 (brt, J=5.6 Hz, 4 H), 3.60–3.70(m, 2H), 3.70–3.80(m, 4 H), 3.90–3.92(m, 2 H), 3.92(s, 4 H), 7.05 (d, J=7.6 Hz, 2 H), 7.49 (d, J=7.6 Hz, 2 H), 7.52 (s, 1 H); MS (ES) m/z: 416.0 (MH$^+$, 100%); HRMS Calcd. for $C_{21}H_{25}N_3O_4S$ (M$^+$): 415.1565. Found: 415.1570.

Intermediate 27

5-[4-(1,4-Dioxa-8-aza-spiro[4.5]dec-8-yl)-benzylidene]-2-(4-methyl-piperazin-1-yl-thiazol-4-one:

The title compound was prepared from 5-[4-(1,4-dioxa-8-aza-spiro[4,5]dec-8-yl)benzylidene]-2-methylsulfanyl-thiazo-4-one(which was obtained in Intermediate 16) and 4-methylpiperazine according to the procedure of Intermediate 17 as a yellowish solid (one major isomer); $^1$H NMR (300 MHz, DMSO-d$_6$) δ 1.68 (brt, J=5.6 Hz, 4 H), 2.22(s, 3 H), 2.40–2.50(m, 4 H), 3.41 (brt, J=5.6 Hz, 4 H), 3.60–3.65 (m, 2H), 3.90–4.05(m, 2 H), 4.05(s, 4 H), 7.05 (d, J=8.7 Hz, 2 H), 7.46 (d, J=8.7 Hz, 2 H), 7.53 (s, 1 H); MS (ES) m/z: 429.0 (MH$^+$, 100%); HRMS Calcd. for $C_{22}H_{28}N_4O_3S$ (M$^+$): 428.1882. Found: 428.1869.

Intermediate 28

1-[4-(2-Morpholin-4-yl-4-oxo-4H-thiazol-5-ylidenemethyl)-phenyl]-piperidin-4-one:

The title compound was prepared from 5-[4-(1,4-dioxa-8-aza-spiro[4.5]dec-8-yl)-benzylidene]-2-morpholin-4-yl-thiazol-4-one(which was obtained in Intermediate 26) according to the procedure of Intermediate 18 as a yellowish solid (one major isomer); $^1$H NMR (300 MHz, DMSO-d$_6$) δ 2.44 (t, J=6.0 Hz, 4 H), 3.60–3.80(m, 10 H), 3.85–3.95(m, 2 H), 7.10 (d, J=8.9 Hz, 2 H), 7.51 (d, J=8.9 Hz, 2 H), 7.57 (s, 1 H); MS (ES) m/z: 372.0 (MH$^+$, 100%); HRMS Calcd. for $C_{19}H_{21}N_3O_3S$ (M$^+$): 371.1303. Found: 371.1310.

Intermediate 29

1-{4-[2-(4-Methyl-piperazin-1-yl)-4-oxo-4H-thiazol-5-ylidenemethyl]-phenyl}-piperidin-4-one:

The title compound was prepared from 5-[4-(1,4-dioxa-8-aza-spiro[4.5]dec-8-yl)-benzylidene]-2-(4-methyl-piperazin-1-yl)-thiazol-4-one(which was obtained in Intermediate 27) according to the procedure of Intermediate 18 as a yellowish solid (one major isomer); $^1$H NMR (300 MHz, DMSO-d$_6$) δ 2.24(s, 3 H), 2.40–2.60(m, 8 H), 3.60–3.70(m, 2 H), 3.74(t, J=6.0 Hz, 4 H), 3.85–3.95(m, 2 H), 7.10 (d, J=8.9 Hz, 2 H), 7.51 (d, J=8.9 Hz, 2 H), 7.55 (s, 1 H); MS (ES) m/z: 385.0 (MH$^+$, 100%); HRMS Calcd. for $C_{20}H_{24}N_4O_2S$ (M$^+$): 384.1620. Found: 384.1616.

Intermediate 30

5-[4-(1,4-Dioxa-8-aza-spiro[4.5]dec-8-yl)-benzylidene]-2-hexylamino-thiazol-4-one:

The title compound was prepared from 5-[4-(1,4-dioxa-8-aza-spiro[4,5]dec-8-yl)benzylidene]-2-methylsulfanyl-thiazo-4-one(which was obtained in Intermediate 16) and hexylamine according to the procedure of Intermediate 17 as a yellowish solid (one major isomer); $^1$H NMR (300 MHz, DMSO-d$_6$) δ 0.87 (t, J=6.6 Hz, 3 H), 1.20–1.40(m, 6 H), 1.50–1.60(m, 2 H), 1.66 (brt, J=5.6 Hz, 4 H), 3.40–3.60(m, 6 H), 3.92(s, 4 H), 7.06 (d, J=8.9 Hz, 2 H), 7.39 (d, J=8.9 Hz, 2 H), 7.48 (s, 1 H), 9.50(brs, 1 H); MS (ES) m/z: 430.0 (MH$^+$, 100%); HRMS Calcd. for $C_{23}H_{31}N_3O_3S$ (M$^+$): 429.2086. Found: 429.2081.

Intermediate 31

2-(3-Dimethylamino-propylamino)-5-[4-(1,4-dioxa-8-aza-spiro[4.5]dec-8-yl)-benzylidene]-thiazol-4-one:

The title compound was prepared from 5-[4-(1,4-dioxa-8-aza-spiro[4,5]dec-8-yl)-benzylidene]-2-methylsulfanyl-thiazo-4-one(which was obtained in Intermediate 16) and 3-dimethylaminopropylamine according to the procedure of Intermediate 17 as a yellowish solid (one major isomer); $^1$H NMR (300 MHz, DMSO-d$_6$) δ 1.60–1.70(m, 6 H), 2.10(s, 6 H), 2.25 (t, J=7.0 Hz, 2 H), 3.30–3.50(m, 6 H), 3.85(s, 4 H), 7.07 (d, J=9.0 Hz, 2 H), 7.40 (d, J=9.0 Hz, 2 H), 7.48 (s, 1 H), 9.50(brs, 1 H); MS (ES) m/z: 431.1 (MH$^+$, 100%); HRMS Calcd. for $C_{22}H_{30}N_4O_3S$ (M$^+$): 430.2038. Found: 430.2040.

Intermediate 32

1-[4-(2-Hexylamino-4-oxo-4H-thiazol-5-ylidenemethyl)-phenyl]-piperidin-4-one:

The title compound was prepared from 5-[4-(1,4-dioxa-8-aza-spiro[4.5]dec-8-yl)benzylidene]-2-hexylamino-thiazol-4-one(which was obtained in Intermediate 30) according to the procedure of Intermediate 18 as a yellowish solid (one major isomer); $^1$H NMR (300 MHz, DMSO-d$_6$) δ 0.87(t, J=6.5 Hz, 3 H), 1.20–1.40(m, 6 H), 1.50–1.75(m, 2 H), 2.43(t, J=5.9 Hz, 4 H), 3.40–3.55(m, 2 H), 3.74 (t, J=5.9 Hz, 4 H), 7.12 (d, J=8.9 Hz, 2 H), 7.44 (d, J=8.9 Hz, 2 H), 7.50 (s, 1 H), 9.47(t, J=5.3 Hz, 1 H); MS (ES) m/z: 386.0 (MH$^+$, 100%); HRMS Calcd. for $C_{21}H_{27}N_3O_2S$ (M$^+$): 385.1824. Found: 385.1809.

Intermediate 33

1-{4-[2-(3-Dimethylamino-propylamino)-4-oxo-4H-thiazol-5-ylidenemethyl]-phenyl}-piperidin-4-one:

The title compound was prepared from 2-(3-dimethylamino-propylamino)-5-[4-(1,4-dioxa-8-aza-spiro[4.5]dec-8-yl)-benzylidene]-thiazol-4-one(which was obtained in Intermediate 31) according to the procedure of Intermediate 18 as a yellowish solid (one major isomer); $^1$H NMR (300 MHz, DMSO-d$_6$) δ 1.60–1.80(m, 2 H), 2.24(s, 6 H), 2.30–2.45(m, 6 H), 3.51 (t, J=6.9 Hz, 2 H), 3.74 (t, J=5.9 Hz, 4 H), 7.12 (d, J=9.0 Hz, 2 H), 7.44 (d, J=9.0 Hz, 2 H), 7.53 (s, 1 H); MS (ES) m/z: 387.0 (MH$^+$, 100%); HRMS Calcd. for $C_{20}H_{26}N_4O_2S$ (M$^+$): 386.1776. Found: 386.1768.

Intermediate 34

(2S)-2-{5-[4-(1,4-Dioxa-8-aza-spiro[4.5]dec-8-yl)-benzylidene]-4-oxo-4,5-dihydro-thiazol-2-ylamino}-pentanedioic acid diethyl ester:

The title compound was prepared from 5-[4-(1,4-dioxa-8-aza-spiro[4,5]dec-8-yl)-benzylidene]-2-methylsulfanyl-thiazo-4-one (which was obtained in Intermediate 16) and diethyl L-glutamate hydrochloride according to the procedure of Intermediate 24 as a yellowish solid (one major isomer); $^1$H NMR (300 MHz, DMSO-d$_6$) δ 1.17(t, J=7.1 Hz, 3 H), 1.21 (t, J=7.1 Hz, 3 H), 1.68(brt, J=5.6 Hz, 4 H), 3.45(brt, J=5.6 Hz, 4 H), 3.91(s, 4H), 4.05(q, J=7.1 Hz, 2 H), 4.15(q, J=7.1 Hz, 2 H), 4.60–4.70(m, 1 H), 7.07 (d, J=9.0 Hz, 2 H), 7.42 (d, J=9.0 Hz, 2 H), 7.52 (s, 1 H); MS (ES) m/z:532.0 (MH$^+$, 100%); HRMS Calcd. for $C_{26}H_{33}N_3O_7S$ (MH$^+$): 532.2117. Found: 532.2115.

Intermediate 35
5-[4-(1,4-Dioxa-8-aza-spiro[4.5]dec-8-yl)-benzylidene]-4-oxo-4,5-dihydro-thiazol-2-yl-cyanamide:

The title compound was prepared from 5-[4-(1,4-dioxa-8-aza-spiro[4,5]dec-8-yl)-benzylidene]-2-methylsulfanyl-thiazo-4-one(which was obtained in Intermediate 16) and cyanamide according to the procedure of Intermediate 24 as a red solid (one major isomer); $^1$H NMR (300 MHz, DMSO-d$_6$) δ 1.68(brt, J=5.6 Hz, 4 H), 3.45(brt, J=5.6 Hz, 4 H), 3.92(s, 4H), 7.05 (d, J=9.0 Hz, 2 H), 7.33(s, 1 H), 7.39 (d, J=9.0 Hz, 2 H); MS (ES) m/z:370.9 (MH$^+$, 100%); HRMS Calcd. for C$_{18}$H$_{19}$N$_4$O$_3$S (MH$^+$): 371.1172. Found: 371.1172.

Intermediate 36
4-Oxo-5-[4-(4-oxo-piperidin-1-yl)-benzylidene]-4,5-dihydro-thiazol-2-yl-cyanamide:

The title compound was prepared from 5-[4-(1,4-dioxa-8-aza-spiro[4.5]dec-8-yl)-benzylidene]-4-oxo-4,5-dihydro-thiazol-2-yl-cyanamide(which was obtained in Intermediate 35) according to the procedure of Intermediate 18 as a red solid (one major isomer); $^1$H NMR (300 MHz, DMSO-d$_6$) δ 2.43(t, J=6.0 Hz, 4 H), 3.76(t, J=6.0 Hz, 4 H), 7.12 (d, J=9.0 Hz, 2 H), 7.36(s, 1 H), 7.47 (d, J=9.0 Hz, 2 H); MS (ES) m/z:326.7 (MH$^+$, 100%); HRMS Calcd. for C$_{16}$H$_{15}$N$_4$O$_2$S (MH$^+$): 327.0910. Found: 327.0909.

Intermediate 37
5-[4-(2,2-Diethoxy-ethoxy)-benzylidene]-2-thioxo-thiazolidin-4-one:

Under nitrogen, a mixture of 4-hydroxybenzaldehyde (1.71 g, 14 mmol), bromoacetaldehyde diethyl acetate (37.4 g, 190 mmol), tetrabutylammonium bromide (0.61 g, 1.9 mmol) and potassium carbonate (26.1 g, 190 mmol) in 100 mL of toluene was refluxed for 2.5 days. After cooling the mixture was dissolved in water and extracted with dichloromethane. The organic layers were dried over magnesium sulfate and concentrated. The residue was purified by column chromatography (eluent: hexanes/ethyl acetate) to give 4-(2,2-diethoxyethoxy) benzaldehyde as a colorless oil (2.60 g, 79%). The title compound was prepared from 4-(2,2-diethoxyethoxy) benzaldehyde and rhodanine according to the procedure of Intermediate 15 as a yellowish solid; $^1$H NMR (300 MHz, DMSO-d$_6$) δ 1.14(t, J=7.1 Hz, 6 H), 3.50–3.80 (m, 4 H), 4.04(d, J=5.0 Hz, 2 H), 4.05–4.30(m, 2 H), 6.06 (t, J=5.0 Hz, 1 H), 7.14 (d, J=9.0 Hz, 2 H), 7.60 (d, J=9.0 Hz, 2 H), 7.63(s, 1 H); MS (ES) m/z:351.7 ((M-H)$^-$, 100%); HRMS Calcd. for C$_{16}$H$_{20}$NO$_4$S$_2$ (MH$^+$): 353.0775. Found: 353.0757.

Intermediate 38
5-[4-(2,2-Diethoxy-ethoxy)-benzylidene]-2-piperidin-1-yl-thiazol-4-one:

A mixture of 5-[4-(2,2-diethoxy-ethoxy)-benzylidene]-2-thioxo-thiazolidin-4-one (which was obtained in Intermediate 37)(1.19 g, 5 mmol), rhodanine (0.67 g, 5 mmol) and piperidine (1.72 g, 20.2 mmol) in ethanol (50 mL) was refluxed for 2 hours. After cooling to room temperature hexanes (70 mL) were added and the solid which was formed was collected to give the title compound as a yellowish solid (1.4 g, 69%); $^1$H NMR (300 MHz, DMSO-d$_6$) δ 1.14(t, J=7.1 Hz, 6 H), 1.55–1.75(m, 6 H), 3.40–3.80 (m, 6 H), 3.85–3.95(m, 2 H), 4.02(d, J=5.2 Hz, 2 H), 4.82 (t, J=5.2 Hz, 1 H), 7.11 (d, J=7.6 Hz, 2 H), 7.57 (d, J=7.6 Hz, 2 H), 7.58(s, 1 H); MS (ES) m/z: 404.9 (MH$^+$, 100%); HRMS Calcd. for C$_{21}$H$_{28}$N$_2$O$_4$S (M$^+$): 404.1770. Found: 404.1780.

Intermediate 39
4-(4-Oxo-2-piperidin-1-yl-4H-thiazol-5-ylidenemethyl)-phenoxy]-acetaldehyde hydrate:

The title compound was prepared from 5-[4-(2,2-diethoxy-ethoxy)-benzylidene]-2-piperidin-1-yl-thiazol-4-one(which was obtained in Intermediate 38) according to the procedure of Intermediate 18 as a yellowish solid; $^1$H NMR (300 MHz, DMSO-d$_6$) δ 1.50–1.75(m, 6 H), 3.55–3.70 (m, 2 H), 3.80–3.95(m, 4 H), 5.05–5.65(m, 1 H), 6.12(d, J=6.6 Hz, 2 H), 7.07 (d, J=9.0 Hz, 2 H), 7.57 (d, J=9.0 Hz, 2 H), 7.58(s, 1 H); MS (ES) m/z: 348.9 ((M+H$_2$O+H)$^+$, 100%); HRMS Calcd. for C$_{17}$H$_{18}$N$_2$O$_3$S (M$^+$): 330.1038. Found: 330.1040.

Intermediate 40
5-[4-(4-Oxo-pyridin-1-yl)-benzylidene]-2-hydroxyamino-thiazo-4-one The title compound was prepared from 5-[4-(1,4-ioxa-8-aza-spiro[4,5]dec-8-yl)benzylidene]-2-hydroxyamino-thiazol-4-one(which was obtained in Intermediate 24) according to the procedure of Intermediate 18 as a yellowish solid (one major isomer); MS (ES) m/z: 318.2 (MH$^+$, 100%).

The following procedures describe the preparation of representative examples of this invention.

EXAMPLE 1
4-((2S)-2-Hydroxy-3-{1-[4-(2-methylamino-4-oxo-4H-thiazol-5-ylidenemethyl)-phenyl]-piperidin-4-ylamino}-propoxy)-1,3-dihydrobenzoimidazol-2-one:

1-[4-(2-Methylamino-4-oxo-4H-thiazol-5-ylidenemethyl)-phenyl]-piperidin-4-one (which was obtained in Intermediate 18)(0.15 g, 0.47 mmol) and (S)-4-[2-hydroxy-3-aminopropoxy]-1,3-dihydro-2H-benzimidazol-2-one (Jesudason, C. D., et al., EP 0 764 640) (0.11 g, 0.47 mmol) were mixed in dimethylformamide (15 mL) and then treated with sodium triacetoxyborohydride (0.16 g, 0.75 mmol) and acetic acid (0.15 mL). After stirring at room temperature under a nitrogen atmosphere for one day the mixture was poured into a saturated aqueous sodium bicarbonate solution. The precipitate was collected and purified by column chromatography (eluent: methanol/methylene chloride) to give the title compound as a pale yellowish solid(0.16 g, 65%); mp>160° C. (dec.); $^1$H NMR (300 MHz, DMSO-d$_6$) δ 1.20–1.45 (m, 2 H), 1.75–2.00 (m, 2 H), 2.60–3.00 (m, 5 H), 3.05 (s, 3 H), 3.75–4.15 (m, 5 H), 6.57 (d, J=7.8 Hz, 1 H), 6.62 (d, J=8.1 Hz, 1 H), 6.87 (t, J=8.1 Hz, 1 H), 7.02 (d, J=8.7 Hz, 2 H), 7.38 (d, J=8.7 Hz, 2 H), 7.47 (s, 1 H), 10.56 (s, 1 H), 10.70 (brs, 1 H); MS (ES) m/z: 262.1 ((M+2H)$^{2+}$, 100%); 522.9 (MH$^+$, 75%); HRMS Calcd. for C$_{26}$H$_{31}$N$_6$O$_4$S (MH$^+$): 523.2128. Found: 523.2142.

EXAMPLE 2
4-[(2S)-2-Hydroxy-3-(1-{4-[2-(2-morpholin-4-ylethylamino)-4-oxo-4H-thiazol-5-ylidenemethyl]-phenyl}-piperidin-4-ylamino)-propoxy]-1,3-dihydrobenzoimidazol-2-one:

The title compound was prepared from 1-{4-[2-(2-morpholin-4-ylethylamino)-4-oxo-4H-thiazol-5-ylidenemethyl]-phenyl}-piperidin-4-one(which was obtained in Intermediate 20) and (S)-4-[2-hydroxy-3-aminopropoxy]-1,3-dihydro-2H-benzimidazol-2-one (Jesudason, C. D., et al., EP 0 764 640) according to the procedure of Example 1 as a pale yellowish solid; mp>140° C. (dec.); $^1$H NMR (300 MHz, DMSO-d$_6$) δ 1.20–1.45 (m, 2 H), 1.75–2.00 (m, 2 H), 2.43 (t, J=4.7 Hz, 2 H), 2.50–3.70 (m, 13 H), 3.59 (t, J=4.7 Hz, 2 H), 3.75–4.15 (m, 5 H), 4.86

(brs, 1 H), 6.57 (d, J=7.5 Hz, 1 H), 6.62 (d, J=7.5 Hz, 1 H), 6.87 (t, J=8.1 Hz, 1 H), 7.02 (d, J=9.0 Hz, 2 H), 7.38 (d, J=9.0 Hz, 2 H), 7.47 (s, 1 H), 9.47 (s, 1 H), 10.57 s, 1 H), 10.70 (brs, 1 H); MS (ES) m/z: 311.5 ((M+2H)$^{2+}$, 100%); 621.9 (MH$^+$, 15%); HRMS Calcd. for $C_{31}H_{40}N_7O_5S$ (MH$^+$): 622.2812. Found: 622.2811.

EXAMPLE 3

4-[(2S)-3-(1-{4-[2-(1-Benzyl-piperidin-4-ylamino)-4-oxo-4H-thiazol-5-ylidenemethyl]-phenyl}-piperidin-4-ylamino)-2-hydroxy-propoxy]-1,3-dihydro-benzoimidazol-2-one:

The title compound was prepared from 1-{4-[2-(1-benzyl-piperdin-4-ylamino)-4-oxo-4H-thiazol-5-ylidenemethyl]-phenyl}-piperidin-4-one(which was obtained in Intermediate 21) and (S)-4-[2-hydroxy-3-aminopropoxy]-1,3-dihydro-2H-benzimidazol-2-one (Jesudason, C. D., et al., EP 0 764 640) according to the procedure of Example 1 as a pale yellowish solid; mp>165° C. (dec.); $^1$H NMR (300 MHz, DMSO-d$_6$) δ 1.20–1.40 (m, 2 H), 1.40–1.65 (m, 2 H), 1.70–2.00 (m, 4 H), 2.06 (brt, J=9.9 Hz, 2 H), 2.55–2.95 (m, 6 H), 3.47 (s, 2 H), 3.75–4.05 (m, 5 H), 4.87 (brs, 1 H), 6.57 (d, J=7.5 Hz, 1 H), 6.61 (d, J=8.1 Hz, 1 H), 6.84 (t, J=8.1 Hz, 1 H), 7.02 (d, J=9.0 Hz, 2 H), 7.20–7.50 (m, 8 H), 9.46 (brs, 1 H), 10.57 (s, 1 H), 10.70 (brs, 1 H); MS (ES) m/z: 341.6 ((M+2H)$^{2+}$, 100%); 682.1 (MH$^+$, 5%); HRMS Calcd. for $C_{37}H_{44}N_7O_4S$ (MH$^+$): 682.3176. Found: 682.3211.

EXAMPLE 4

2-(1-Benzyl-piperidin-4-ylamino)-5-(4-{(2S)-4-[2-hydroxy-3-(4-hydroxy-phenoxy)-propylamino]-piperidin-1-yl}-benzylidene)-thiazol-4-one:

The title compound was prepared from 1-{4-[2-(1-benzyl-piperdin-4-ylamino)-4-oxo-4H-thiazol-5-ylidenemethyl]-phenyl}-piperidin-4-one (which was obtained in Intermediate 21) and 4-[(2S)-3-amino-2-hydroxy-propoxyl]-phenol (which was obtained in Intermediate 5) according to the procedure of Example 1 as a pale yellowish solid; mp>175° C. (dec.); $^1$H NMR (300 MHz, DMSO-d$_6$) δ 1.20–1.40 (m, 2 H), 1.40–1.65 (m, 2 H), 1.70–2.00 (m, 4 H), 2.06 (brt, J=9.5 Hz, 2 H), 2.55–2.95 (m, 6 H), 3.47 (s, 2 H), 3.70–4.00 (m, 5 H), 4.92 (brs, 1 H), 6.66 (d, J=6.8 Hz, 2 H), 6.75 (d, J=6.8 Hz, 2 H), 7.02 (d, J=9.0 Hz, 2 H), 7.20–7.50 (m, 8 H), 8.89 (brs, 1 H), 9.29 (brs, 1 H); MS (ES) m/z:321.6 ((M+2H)$^{2+}$, 100%); 642.1 (MH$^+$, 5%); HRMS Calcd. for $C_{36}H_{44}N_5O_4S$ (MH$^+$): 642.3114. Found: 642.3095.

EXAMPLE 5

N-{5-[2-(1-{4-[2-(1-Benzyl-piperidin-4-ylamino)-4-oxo-4H-thiazol-5-ylidenemethyl]-phenyl}-piperidin-4-ylamino)-1-hydroxy-ethyl]-2-hydroxy-phenyl}-methanesulfonamide:

The title compound was prepared from 1-{4-[2-(1-benzyl-piperdin-4-ylamino)-4-oxo-4H-thiazol-5-ylidenemethyl]-phenyl}-piperidin-4-one (which was obtained in Intermediate 21) and N-[5-(2-amino-1-hydroxy-ethyl)-2-hydroxy-phenyl]-methanesulfonamide (which was obtained in Intermediate 9) according to the procedure of Example 1 as a pale yellowish solid; mp>210° C. (dec.); $^1$H NMR (300 MHz, DMSO-d$_6$) δ 1.20–1.40 (m, 2 H), 1.40–1.65 (m, 2 H), 1.70–2.00 (m, 4 H), 2.06 (brt, J=9.8 Hz, 2 H), 2.50–3.50 (m, 6 H), 2.92 (s, 3 H), 3.47 (s, 2 H), 3.70–4.00 (m, 2 H), 4.47 (dd, J=7.9, 4.3 Hz, 1 H), 6.81 (d, J=8.2 Hz, 1 H), 6.95–7.05 (m, 2 H), 7.17 (d, J=1.9 Hz, 1 H), 7.20–7.55 (m, 8 H); MS (ES) m/z:353.1 ((M+2H)$^{2+}$, 100%); 705.1 (MH$^+$, 5%); HRMS Calcd. for $C_{36}H_{45}N_6O_5S_2$ (MH$^+$): 705.2893. Found: 705.2921.

EXAMPLE 6

N'-[5-(4-{4-[(2S)-2-Hydroxy-3-(2-oxo-2,3-dihydro-1H-benzoimidazol-4-yloxy)-propylamino]-piperidin-1-yl}-benzylidene)-4-oxo-4,5-dihydro-thiazol-2-yl]-N,N-dimethyl-guanidine:

The title compound was prepared from N,N-dimethyl-4-N'-{4-oxo-5-[4-(4-oxo-piperidin-1-yl)-benzylidene]-4,5-dihydro-thiazol-2-yl}-guanidine (which was obtained in Intermediate 23) and (S)-4-[2-hydroxy-3-aminopropoxy]-1,3-dihydro-2H-benzimidazol-2-one (Jesudason, C. D., et al., EP 0 764 640) according to the procedure of Example 1 as a pale yellowish solid; mp>165° C. (dec.); $^1$H NMR (300 MHz, DMSO-d$_6$) δ 1.20–1.40 (m, 2 H), 1.70–2.00 (m, 4 H), 2.50–3.00 (m, 5 H), 3.33 (s, 6 H), 3.70–4.10 (m, 5 H), 4.86 (brs, 1 H), 6.56 (d, J=7.5 Hz, 1 H), 6.61 (d, J=8.1 Hz, 1 H), 6.88 (t, J=8.1 Hz, 1 H), 7.02 (d, J=9.0 Hz, 2 H), 7.40 (d, J=9.0 Hz, 2 H), 7.47 (s, 1 H), 10.57 (s, 1 H), 10.70 (brs, 1 H); MS (ES) m/z: 290.0 ((M+2H)$^{2+}$, 100%); 579.1 (MH$^+$, 5%); HRMS Calcd. for $C_{28}H_{35}N_8O_4S$ (MH$^+$): 579.2502. Found: 579.2534.

EXAMPLE 7

N-{5-[2-(1-{4-[2-(N',N'-Dimethyl-guanidino)-4-oxo-4H-thiazol-5-ylidenemethyl]-phenyl}-piperidin-4-ylamino)-1-hydroxy-ethyl]-2-hydroxy-phenyl}-methanesulfonamide:

The title compound was prepared from N,N-dimethyl-4-N'-{4-oxo-5-[4-(4-oxo-piperidin-1-yl)-benzylidene]-4,5-dihydro-thiazol-2-yl}-guanidine (which was obtained in Intermediate 23) and N-[5-(2-amino-1-hydroxy-ethyl)-2-hydroxy-phenyl]-methanesulfonamide (which was obtained in Intermediate 9) according to the procedure of Example 1 as a pale yellowish solid; mp>145° C. (dec.); $^1$H NMR (300 MHz, DMSO-d$_6$) δ 1.20–1.40 (m, 2 H), 1.70–2.00 (m, 2 H), 2.00–3.50 (m, 5 H), 2.91 (s, 6 H), 3.70–3.90 (m, 2 H), 4.48 (dd, J=7.9, 4.3 Hz, 1 H), 6.81 (d, J=8.3Hz, 1 H), 6.95–7.10 (m, 3 H), 7.18 (d, J=2.0 Hz, 1 H), 7.41 (d, J=8.9 Hz, 2 H), 7.47 (s, 1 H); $C_{27}H_{36}N_7O_5S_2$ (MH$^+$): 602.2219. Found: 602.2225.

EXAMPLE 8

3-[5-(4-{4-[(2S)-2-Hydroxy-3-(2-oxo-2,3-dihydro-1H-benzoimidazol-4-yloxy)-propylamino]-piperidin-1-yl}-benzylidene)-4-oxo-4,5-dihydro-thiazol-2-ylamino]-propionic acid ethyl ester:

The title compound was prepared from 3-[5-(4-oxo-piperidin-1-yl)-benzylidene-4-oxo-4,5-dihydrothiazol-2-ylamino]-propionic acid ethyl ester (which was obtained in Intermediate 22) and (S)-4-[2-hydroxy-3-aminopropoxy]-1,3-dihydro-2H-benzimidazol-2-one (Jesudason, C. D., et al., EP 0 764 640) according to the procedure of Example 1 as a pale yellowish solid; mp>120° C. (dec.); $^1$H NMR (300 MHz, DMSO-d$_6$) δ 1.19 (t, J=7.1 Hz, 3 H), 1.20–1.40 (m, 2 H), 1.85–2.00 (m, 2 H), 2.50–3.00 (m, 7H), 3.50–4.10 (m, 7 H), 4.10 (q, J=7.1 Hz, 2 H), 6.57 (d, J=7.8 Hz, 1 H), 6.61 (d, J=8.4 Hz, 1 H), 6.82 (t, J=8.1 Hz, 1 H), 7.04 (d, J=7.8 Hz, 2 H), 7.40 (d, J=7.8 Hz, 2 H), 7.47 (s, 1 H), 10.58 (s, 1 H), 10.71 (brs, 1 H); MS (ES) m/z: 305.0 ((M+2H)$^{2+}$, 100%); 609.1 (MH$^{30}$, 20%); HRMS Calcd. for $C_{30}H_{37}N_6O_6S$ (MH$^+$): 609.2495. Found: 609.2486.

EXAMPLE 9

3-[5-(4-{4-[(2S)-2-Hydroxy-3-(2-oxo-2,3-dihydro-1H-benzoimidazol-4-yloxy)-propylamino]-piperidin-1-yl}-benzylidene)-4-oxo-4,5-dihydro-thiazol-2-ylamino]-propionic acid:

The title compound was prepared from 3-[5-(4-{4-[(2S)-2-hydroxy-3-(2-oxo-2,3-dihydro-1H-benzoimidazol-4-yloxy)-propylamino]-piperidin-1-yl}-benzylidene)-4-oxo-4,5-dihydro-thiazol-2-ylamino]-propionic acid ethyl ester (which was obtained in Example 8)by NaOH hydrolysis as a pale yellowish solid; MS (ES) m/z: 291.0 ((M+2H)$_{2+}$, 100%); 581.0 (MH$^+$, 30%); HRMS Calcd. for C$_{28}$H$_{33}$N$_6$O$_6$S (MH$^+$): 581.2182. Found: 581.2195.

EXAMPLE 10
4-((2S)-2-Hydroxy-3-{1-[4-(2-hydroxyamino-4-oxo-4H-thiazol-5-ylidenemethyl)-phenyl]-piperidin-4-ylamino}-propoxy)-1,3-dihydro-benzoimidazol-2-one:

The title compound was prepared from 5-[4-(4-oxo-pyridin-1-yl)-benzylidene]-2-hydroxyamino-thiazo-4-one (which was obtained in Intermediate 40) and (S)-4-[2-hydroxy-3-aminopropoxy]-1,3-dihydro-2H-benzimidazol-2-one (Jesudason, C. D., et al., EP 0 764 640) according to the procedure of Example 1 as a pale yellowish solid; mp 201–213° C. (dec.); $^1$H NMR (300 MHz, DMSO-d$_6$) δ 1.30–1.45 (m, 2 H), 1.85–2.00 (m, 2 H), 2.60–3.00 (m, 5 H), 3.60–4.10 (m, 5 H), 6.57 (d, J=7.7 Hz, 1 H), 6.62 (d, J=8.2 Hz, 1 H), 6.88 (t, J=8.1 Hz, 1 H), 7.04 (d, J=9.0 Hz, 2 H), 7.36 (s, 1 H), 7.42 (d, J=9.0 Hz, 2 H), 10.50–10.70 (m, 2 H); MS (ES) m/z: 525.0 (MH$^+$); HRMS Calcd. for C$_{25}$H$_{29}$N$_6$O$_5$S (MH$^+$): 525.1920. Found: 525.1914.

EXAMPLE 11
N-[2-Hydroxy-5-(1-hydroxy-2-{1-[4-(2-hydroxyamino-4-oxo-4H-thiazol-5-ylidenemethyl)-phenyl]-piperidin-4-ylamino}-ethyl)-phenyl]-methanesulfonamide:

The title compound was prepared from 5-[4-(4-oxo-pyridin-1-yl)-benzylidene]-2-hydroxyamino-thiazo-4-one (which was obtained in Intermediate 40) and N-[5-(2-amino-1-hydroxy-ethyl)-2-hydroxy-phenyl]-methanesulfonamide (which was obtained in Intermediate 9) according to the procedure of Example 1 as a pale yellowish solid; mp>190° C. (dec.); $^1$H NMR (300 MHz, DMSO-d$_6$) δ 1.25–1.45 (m, 2 H), 1.70–2.00 (m, 2 H), 2.50–3.00 (m, 5 H), 2.98 (s, 3 H), 3.80–3.90 (m, 2 H), 4.50 (dd, J=8.2 4.1 Hz, 1 H), 6.83 (d, J=8.1 Hz, 1 H), 6.95–7.10 (m, 3 H), 7.18 (d, J=1.8 Hz, 1 H), 7.36 (s, 1 H), 7.39 (d, J=6.6 Hz, 2 H); MS (ES) m/z: 547.9 (MH$^+$); HRMS Calcd. for C$_{24}$H$_{30}$N$_5$O$_6$S$_2$ (MH$^+$): 548.1638. Found: 548.1663.

EXAMPLE 12
4-((2S)-2-Hydroxy-3-{1-[4-(4-oxo-2-piperidin-1-yl-4H-thiazol-5-ylidenemethyl)-phenyl]-piperidin-4-ylamino}-propoxy)-1,3-dihydro-benzoimidazol-2-one:

The title compound was prepared from 1-[4-(4-oxo-2-piperidin-1-yl-4H-thiazol-5-ylidenemethyl)-phenyl]-piperidin-4-one (which was obtained in Intermediate 25) and (S)-4-[2-hydroxy-3-aminopropoxy]-1,3-dihydro-2H-benzimidazol-2-one (Jesudason, C. D., et al., EP 0 764 640) according to the procedure of Example 1 as a pale yellowish solid; mp>140° C. (dec.); $^1$H NMR (300 MHz, DMSO-d$_6$) δ 1.20–1.40 (m, 2 H), 1.55–1.75 (m, 6 H), 1.80–2.00 (m, 2 H), 2.60–2.95 (m, 5 H), 3.50–4.10 (m, 9 H), 4.89 (brs, 1 H), 6.57 (d, J=7.8 Hz, 1 H), 6.62 (d, J=8.2 Hz, 1 H), 6.87 (t, J=8.1 Hz, 1 H), 7.01 (d, J=8.9 Hz, 2 H), 7.45 (d, J=8.9 Hz, 2 H), 7.51 (s, 1 H), 10.60 (s, 1 H), 10.70 (brs, 1 H); MS (ES) m/z: 289.1 ((M+2H)$^{2+}$, 100%), 577.1 (MH$^+$, 50%); HRMS Calcd. for C$_{30}$H$_{37}$N$_6$O$_4$S (MH$^+$): 577.2597. Found: 577.2625.

EXAMPLE 13
N-[2-Hydroxy-5-((1R)-1-hydroxy-2-{1-[4-(4-oxo-2-piperidin-1-yl-4H-thiazol-5-ylidenemethyl)-phenyl]-piperidin-4-ylamino}-ethyl)-phenyl]-methanesulfonamide:

The title compound was prepared from 1-[4-(4-oxo-2-piperidin-1-yl-4H-thiazol-5-ylidenemethyl)-phenyl]-piperidin-4-one (which was obtained in Intermediate 25) and N-[5-(2-amino-(1R)-1-hydroxy-ethyl)-2-hydroxy-phenyl]-methanesulfonamide (which was obtained in Intermediate 10) according to the procedure of Example 1 as a pale yellowish solid; mp>120° C. (dec.); $^1$H NMR (300 MHz, DMSO-d$_6$) δ 1.20–1.40 (m, 2 H), 1.55–1.75 (m, 6 H), 1.80–2.00 (m, 2 H), 2.60–3.00 (m, 5 H), 2.92 (s, 3 H), 3.50–3.90 (m, 6 H), 4.49 (dd, J=8.0, 4.2 Hz, 1 H), 6.82 (d, J=8.5 Hz, 1 H), 6.95–7.07 (m, 3 H), 7.18 (d, J=2.0 Hz, 1 H), 7.45 (d, J=8.9 Hz, 2 H), 7.50 (s, 1 H); MS (ES) m/z: 300.6 ((M+2H)$^{2+}$, 100%), 600.1 (MH$^+$, 50%); HRMS Calcd. for C$_{29}$H$_{37}$N$_5$O$_5$S$_2$ (MH$^+$): 600.2314. Found: 600.2330.

EXAMPLE 14
N-[2-Hydroxy-5-((2S)-2-hydroxy-3-{1-[4-(4-oxo-2-piperidin-1-yl-4H-thiazol-5-ylidenemethyl)-phenyl]-piperidin-4-ylamino}-propoxy)-phenyl]-methanesulfonamide:

The title compound was prepared from 1-[4-(4-oxo-2-piperidin-1-yl-4H-thiazol-5-ylidenemethyl)-phenyl]-piperidin-4-one (which was obtained in Intermediate 25) and N-[5-((2S)-3-amino-2-hydroxy-propoxy)-2-hydroxy-phenyl]-methanesulfonamide (which was obtained in Intermediate 14) according to the procedure of Example 1 as a yellowish solid; mp>95° C. (dec.); $^1$H NMR (300 MHz, DMSO-d$_6$) δ 1.20–1.40 (m, 2 H), 1.55–1.70 (m, 6 H), 1.85–2.00 (m, 2 H), 2.55–2.90 (m, 6 H), 2.92 (s, 3 H), 3.60 (br s, 2 H), 3.70–3.95 (m, 6 H), 6.61 (dd, J=8.8, 2.9 Hz, 1 H), 6.75–6.80 (m, 2 H), 7.02 (d, J=9.0 Hz, 2 H), 7.45 (d, J=9.0 Hz, 2 H), 7.50 (s, 1 H); MS (ES) m/z: 315.6 ((M+2H)$^{2+}$, 100%); 630.1 (MH$^+$, 100%); HRMS Calcd. for C$_{30}$H$_{40}$N$_5$O$_6$S$_2$ (MH$^+$): 630.2420. Found: 630.2397.

EXAMPLE 15
8-Hydroxy-5-((2S)-2-hydroxy-3-{1-[4-(4-oxo-2-piperidin-1-yl-4H-thiazol-5-ylidenemethyl)-phenyl]-piperidin-4-ylamino}-propoxy)-3,4-dihydro-1H-quinolin-2-one:

The title compound was prepared from 1-[4-(4-oxo-2-piperidin-1-yl-4H-thiazol-5-ylidenemethyl)-phenyl]-piperidin-4-one (which was obtained in Intermediate 25) and 5-((2S)-3-amino-2-hydroxy-propoxy)-8-hydroxy-3,4-dihydro-1H-quinolin-2-one (which was obtained in Intermediate 12) according to the procedure of Example 1 as a yellowish solid; mp>120° C. (dec.); $^1$H NMR (300 MHz, DMSO-d$_6$) δ 1.20–1.40 (m, 2 H), 1.55–1.70 (m, 6 H), 1.85–2.00 (m, 2 H), 2.43 (t, J=7.9 Hz, 2.55–2.90 (m, 9 H), 3.60 (br s, 2 H), 3.70–3.95 (m, 6 H), 6.44 (d, J=9.0 Hz, 1 H), 6.69 (d, J=9.0 Hz, 1 H), 7.02 (d, J=9.0 Hz, 2 H), 7.44 (d, J=9.0 Hz, 2 H), 7.50 (s, 1 H), 8.82 (s, 1 H); MS (ES) m/z: 303.6 ((M+2H)$^{2+}$, 100%); 606.1 (MH$^+$, 10%); HRMS Calcd. for C$_{32}$H$_{40}$N$_5$O$_5$S (MH$^+$): 606.2750. Found: 606.2711.

EXAMPLE 16
5-(4-{4-[(2S)-2-Hydroxy-3-(4-hydroxy-phenoxy)-propylamino]-piperidin-1-yl}-benzylidene)-2-piperidin-1-yl-thiazol-4-one:

The title compound was prepared from 1-[4-(4-oxo-2-piperidin-1-yl-4H-thiazol-5-ylidenemethyl)-phenyl]-piperidin-4-one (which was obtained in Intermediate 25) and 4-((2S)-3-amino-2-hydroxy-propoxy)-phenol (which was obtained in Intermediate 5) according to the procedure of Example 1 as a yellowish solid; mp>85° C. (dec.); $^1$H NMR (300 MHz, DMSO-d$_6$) δ 1.20–1.40 (m, 2 H), 1.55–1.70 (m, 6 H), 1.85–2.00 (m, 2 H), 2.55–2.95 (m, 6 H), 3.60 (br s, 2 H), 3.70–3.95 (m, 6 H), 6.66 (d, J=9.0 Hz, 2 H), 6.75 (d, J=9.0 Hz, 2 H), 7.02 (d, J=9.0 Hz, 1 H), 7.48 (d, J=9.0 Hz, 1 H), 7.50 (s, 1 H), 8.90 (brs, 1 H); MS (ES) m/z: 269.0 ((M+2H)$^{2+}$, 100%); 537.6 (MH$^+$, 10%); HRMS Calcd. for C$_{29}$H$_{37}$N$_4$O$_4$S (MH$^+$): 537.2536. Found: 537.2500.

EXAMPLE 17
N'-[5-(4-{4-[(2S)-2-Hydroxy-3-(8-hydroxy-2-oxo-1,2,3,4-tetrahydro-quinolin-5-yloxy)-propylamino]-piperidin-1- yl}-benzylidene)-4-oxo-4,5-dihydro-thiazol-2-yl]-N,N-dimethyl-guanidine:

The title compound was prepared from N,N-dimethyl-N'-{4-oxo-5-[4-(4-oxo-piperidin-1-yl)-benzylidene]-4,5-dihydro-thiazol-2-yl}-guanidine(which was obtained in Intermediate 23) and 5-((2S)-3-amino-2-hydroxy-propoxy)-8-hydroxy-3,4-dihydro-1H-quinolin-2-one (which was obtained in Intermediate 12) according to the procedure of Example 1 as a yellowish solid; mp>140° C. (dec.); $^1$H NMR (300 MHz, DMSO-$d_6$) δ 1.20–1.40 (m, 2 H), 1.80–1.95 (m, 6 H), 2.40 (t, J=7.9 Hz, 2 H), 2.55–3.20 (m, 12 H), 3.70–3.95 (m, 6 H), 6.44 (d, J=8.7 Hz, 1 H), 6.60 (d, J=8.7 Hz, 1 H), 7.00 (d, J=8.9 Hz, 2 H), 7.41 (d, J=8.9 Hz, 2 H), 7.47 (s, 1 H), 8.82 (brs, 1 H); MS (ES) m/z: 304.6 ((M+2H)$^{2+}$, 100%); 608.1 (MH$^+$, 10%); HRMS Calcd. for $C_{30}H_{38}N_7O_5S$ (MH$^+$): 608.2655. Found: 608.2655.

EXAMPLE 18
4-((2S)-2-Hydroxy-3-{1-[4-(2-morpholin-4-yl-4-oxo-4H-thiazol-5-ylidenemethyl)-phenyl]-piperidin-4-ylamino}-propoxy)-1,3-dihydro-benzoimidazol-2-one:

The title compound was prepared from 1-[4-(2-morpholin-4-yl-4-oxo-4H-thiazol-5-ylidenemethyl)-phenyl]-piperidin-4-one(which was obtained in Intermediate 28) and (S)-4-[2-hydroxy-3-aminopropoxy]-1,3-dihydro-2H-benzimidazol-2-one (Jesudason, C. D., et al., EP 0 764 640) according to the procedure of Example 1 as a yellowish solid; mp>150° C. (dec.); $^1$H NMR (300 MHz, DMSO-$d_6$) δ 1.20–1.40 (m, 2 H), 1.80–1.95 (m, 2 H), 2.55–2.95 (m, 4 H), 3.60–4.10 (m, 14 H), 4.90 (br s, 1 H), 6.56 (d, J=7.8 Hz, 1 H), 6.62 (d, J=8.0 Hz, 1 H), 6.87 (dd, J=7.9, 7.9 Hz, 1 H), 7.02 (d, J=8.9 Hz, 2 H), 7.45 (d, J=8.9 Hz, 2 H), 7.54 (s, 1 H), 10.65(s, 1 H), 10.75 (brs, 1 H); MS (ES) m/z: 290.0 ((M+2H)$^{2+}$, 100%); 579.1 (MH$^+$, 80%); HRMS Calcd. for $C_{29}H_{36}N_6O_5S$ (MH$^+$): 579.2390. Found: 579.2392.

EXAMPLE 19
4-[(2S)-2-Hydroxy-3-(1-{4-[2-(4-methyl-piperazin-1-yl)-4-oxo-4H-thiazol-5-ylidenemethyl]-phenyl}-piperidin-4-ylamino)-propoxy]-1,3-dihydro-benzoimidazol-2-one:

The title compound was prepared from 1-{4-[2-(4-methyl-piperazin-1-yl)-4-oxo-4H-thiazol-5-ylidenemethyl]-phenyl}-piperidin-4-one(which was obtained in Intermediate 29) and (S)-4-[2-hydroxy-3-aminopropoxy]-1,3-dihydro-2H-benzimidazol-2-one (Jesudason, C. D., et al., EP 0 764 640) according to the procedure of Example 1 as a yellowish solid; mp>150° C. (dec.); $^1$H NMR (300 MHz, DMSO-$d_6$) δ 1.20–1.40 (m, 2 H), 1.85–2.00 (m, 2 H), 2.24 (s, 3 H), 2.40–3.00 (m, 11H), 3.50–4.10 (m, 7 H), 6.56 (d, J=8.1Hz, 1 H), 6.62 (d, J=8.1Hz, 1 H), 6.84 (dd, J=8.1, 8.1Hz, 1 H), 7.02 (d, J=9.0 Hz, 2 H), 7.48 (d, J=9.0 Hz, 2 H), 7.52 (s, 1 H), 10.3–11.0 (brs, 2 H); MS (ES) m/z: 296.5 ((M+2H)$^{2+}$, 100%); 592.1 (MH$^+$, 20%); HRMS Calcd. for $C_{30}H_{38}N_7O_4S$ (MH$^+$): 592.2760. Found: 592.2685.

EXAMPLE 20
N'-(5-{4-[4-((2S)-2-Hydroxy-3-phenoxy-propylamino)-piperidin-1-yl]-benzylidene}-4-oxo-4,5-dihydro-thiazol-2-yl)-N,N-dimethyl-guanidine:

The title compound was prepared from N,N-dimethyl-N'-{4-oxo-5-[4-(4-oxo-piperidin-1-yl)-benzylidene]-4,5-dihydro-thiazol-2-yl}-guanidine(which was obtained in Intermediate 23) and (2S)-1-amino-3-phenoxy-propan-2-ol (which was obtained in Intermediate 3) according to the procedure of Example 1 as a yellowish solid; mp>205° C. (dec.); $^1$H NMR (300 MHz, DMSO-$d_6$) δ 1.20–1.40 (m, 2 H), 1.75–1.95 (m, 2 H), 2.50–3.70 (m, 9 H), 3.70–4.00 (m, 7 H), 4.95 (brs, 1 H), 6.64–6.94 (m, 3 H), 7.01(d, J=8.9 Hz, 2 H), 7.27–7.30(m, 2 H), 7.41 (d, J=8.9 Hz, 2 H), 7.47 (s, 1 H); MS (ES) m/z: 262.0 ((M+2H)$^{2+}$, 100%); 523.0 (MH$^+$, 10%); HRMS Calcd. for $C_{27}H_{35}N_6O_3S$ (MH$^+$): 523.2491. Found: 523.2511.

EXAMPLE 21
N'-[5-(4-{[(2S)-2-Hydroxy-3-(4-hydroxy-phenoxy)-propylamino]-piperidin-1-yl}-benzylidene)-4-oxo-4,5-dihydro-thiazol-2-yl]-N,N-dimethyl-guanidine:

The title compound was prepared from N,N-dimethyl-N'-{4-oxo-5-[4-(4-oxo-piperidin-1-yl)-benzylidene]-4,5-dihydro-thiazol-2-yl}-guanidine(which was obtained in Intermediate 23) and 4-((2S)-3-amino-2-hydroxy-propoxy)-phenol (which was obtained in Intermediate 5) according to the procedure of Example 1 as a yellowish solid; $^1$H NMR (300 MHz, DMSO-$d_6$) δ 1.20–1.40 (m, 2 H), 1.75–1.95 (m, 2 H), 2.50–3.30 (m, 9 H), 3.70–3.90 (m, 7 H), 4.90 (brs, 1 H), 6.66 (d, J=6.8 Hz, 1 H), 6.74 (d, J=6.8 Hz, 1 H), 7.01 (d, J=8.8 Hz, 2 H), 7.41 (d, J=8.8 Hz, 2 H), 7.47 (s, 1 H); MS (ES) m/z: 270.0 ((M+2H)$^{2+}$, 100%); 539.1 (MH$^+$, 10%); HRMS Calcd. for $C_{27}H_{35}N_6O_4S$ (MH$^+$): 539.2441. Found: 539.2422.

EXAMPLE 22
5-{4-[4-((2S)-2-Hydroxy-3-phenoxy-propylamino)-piperidin-1-yl]-benzylidene}-2-morpholin-4-yl-thiazol-4-one dihydrochloride salt:

The free base was prepared from 1-[4-(2-morpholin-4-yl-4-oxo-4H-thiazol-5-ylidenemethyl)-phenyl]-piperidin-4-one (which was obtained in Intermediate 28) and (2S)-1-amino-3-phenoxy-propan-2-ol (which was obtained in Intermediate 3) according to the procedure of Example 1. The free base was dissolved in methanol/dichloromethane and treated with hydrogen chloride gas. After concentrated the solvents the product was obtained as a yellowish solid; mp>160° C. (dec.); $^1$H NMR (300 MHz, DMSO-$d_6$) δ 1.60–1.90 (m, 2 H), 2.05–2.25 (m, 2 H), 2.80–3.30 (m, 7 H), 3.60–4.40 (m, 11H), 6.90–7.10(m, 3 H), 7.14(d, J=8.7 Hz, 2 H), 7.51 (d, J=8.7 Hz, 2 H), 7.57 (s, 1 H), 8.92(brs, 1 H), 9.36(brs, 1 H); MS (ES) m/z: 262.1 ((M+2H)$^{2+}$, 100%); 523.1(MH$^+$, 30%); HRMS Calcd. for $C_{28}H_{35}N_4O_3S$ (MH$^+$): 523.2379. Found: 523.2394.

EXAMPLE 23
5-(4-{4-[(2S)-2-Hydroxy-3-(4-hydroxy-phenoxy)-propylamino]-piperidin-1-yl}-benzylidene)-2-morpholin-4-yl-thiazol-4-one:

The title compound was prepared from 1-[4-(2-morpholin-4-yl-4-oxo-4H-thiazol-5-ylidenemethyl)-phenyl]-piperidin-4-one(which was obtained in Intermediate 28) and (2S)-1-amino-3-(4-hydroxy-phenoxy)-propan-2-ol (which was obtained in Intermediate 5) according to the procedure of Example 1 as a yellowish solid; mp>100° C. (dec.); $^1$H NMR (300 MHz, DMSO-$d_6$) δ 1.20–1.40 (m, 2 H), 1.80–1.95 (m, 2 H), 2.50–3.00 (m, 7 H), 3.60–4.00 (m, 11H), 6.66(d, J=9.2 Hz, 2 H), 6.74 (d, J=8.9 Hz, 2 H), 7.02(d, J=9.2 Hz, 2 H), 7.45(d, J=8.9 Hz, 2 H), 7.54 (s, 1 H); MS (ES) m/z: 270.0 ((M+2H)$^{2+}$, 100%); 539.1(MH$^+$, 40%); HRMS Calcd. for $C_{28}H_{35}N_4O_5S$ (MH$^+$): 539.2328. Found: 539.2322.

EXAMPLE 24
5-(4-{4-[(2S)-2-Hydroxy-3-(4-hydroxy-phenoxy)-propylamino]-piperidin-1-yl}-benzylidene)-2-(4-methyl-piperazin-1-yl)-thiazol-4-one:

The title compound was prepared from 1-{4-[2-(4-methyl-piperazin-1-yl)-4-oxo-4H-thiazol-5-ylidenemethyl]- phenyl}-piperidin-4-one (which was obtained in Intermediate 29) and (2S)-1-amino-3-(4-hydroxy-phenoxy)-propan-2-ol (which was obtained in Intermediate 5) according to the procedure of Example 1 as a yellowish solid; mp>210° C. (dec.); $^1$H NMR (300 MHz, DMSO-d$_6$) δ 1.20–1.40 (m, 2 H), 1.80–1.95 (m, 2 H), 2.24 (s, 3 H), 2.40–4.00 (m, 18 H), 6.64(d, J=8.9 Hz, 2 H), 6.73 (d, J=8.9 Hz, 2 H), 7.00(d, J=8.9 Hz, 2 H), 7.45(d, J=8.9 Hz, 2 H), 7.52 (s, 1 H), 8.89(brs, 1 H); MS (ES) m/z: 276.6 ((M+2H)$^{2+}$, 100%); 552.0(MH$^+$, 10%); HRMS Calcd. for C$_{29}$H$_{38}$N$_5$O$_4$S (MH$^+$): 552.2645. Found: 552.2634.

EXAMPLE 25

5-(4-{4-[(2R)-2-(3-Chloro-phenyl)-2-hydroxy-ethylamino]-piperidin-1-yl}-benzylidene)-2-morpholin-4-yl-thiazol-4-one:

The title compound was prepared from 1-[4-(2-morpholin-4-yl-4-oxo-4H-thiazol-5-ylidenemethyl)-phenyl]-piperidin-4-one(which was obtained in Intermediate 28) and (1R)-2-amino-1-(3-chloro-phenyl)-ethanol (which was obtained in Intermediate 1) according to the procedure of Example 1 as a yellowish solid; mp>70° C. (dec.); $^1$H NMR (300 MHz, DMSO-d$_6$) δ 1.20–1.40 (m, 2 H), 1.70–1.95 (m, 2 H), 2.60–2.90 (m, 7 H), 3.50–4.00(m, 8 H), 4.55–4.65(m, 1 H), 5.46 (brs, 1H), 7.02 (d, J=9.0 Hz, 2 H), 7.25–7.45 (m, 7 H), 7.54 (s, 1 H); MS (ES) m/z: 527.1(MH+, 100%); HRMS Calcd. for C$_{27}$H$_{32}$ClN$_4$O$_3$S (MH$^+$): 527.1884. Found: 527.1863.

EXAMPLE 26

2-(3-Dimethylamino-propylamino)-5-{4-[4-((2S)-2-hydroxy-3-phenoxy-propylamino)-piperidin-1-yl]-benzylidene}-thiazol-4-one:

The title compound was prepared from 1-{4-[2-(3-dimethylamino-propylamino)-4-oxo-4H-thiazol-5-ylidenemethyl]-phenyl}-piperidin-4-one(which was obtained in Intermediate 33) and (2S)-1-amino-3-phenoxy-propan-2-ol(which was obtained in Intermediate 3) according to the procedure of Example 1 as a yellowish solid; mp 166–168° C. (dec.); $^1$H NMR (300 MHz, DMSO-d$_6$) δ 1.20–1.40 (m, 10 H), 1.60–1.80 (m, 2 H), 1.80–2.00 (m, 2 H), 2.19 (s, 6 H), 2.25 (t, J=6.8 Hz, 2 H), 2.55–3.00(m, 5 H), 3.50–4.05(m, 7 H), 6.65–6.95(m, 3 H), 7.02 (d, J=9.0 Hz, 2 H), 7.20–7.30 (m, 2 H), 7.40 (d, J=9.0 Hz, 2 H), 7.48 (s, 1 H); MS (ES) m/z: 269.6 ((M+2H)$^{2+}$, 100%), 538.1(MH$^+$, 10%); HRMS Calcd. for C$_{29}$H$_{40}$N$_5$O$_3$S (MH$^+$): 538.2852. Found: 538.2885.

EXAMPLE 27

2-Hexylamino-5-{4-[4-((2S)-2-hydroxy-3-phenoxy-propylamino)-piperidin-1-yl]-benzylidene}-thiazol-4-one:

The title compound was prepared from 1-[4-(2-hexylamino-4-oxo-4H-thiazol-5-ylidenemethyl)-phenyl]-piperidin-4-one(which was obtained in Intermediate 32) and (2S)-1-amino-3-phenoxy-propan-2-ol(which was obtained in Intermediate 3) according to the procedure of Example 1 as a yellowish solid; mp 182–184° C. (dec.); 1H NMR (300 MHz, DMSO-d$_6$) δ 0.87(t, J=6.5 Hz, 3 H), 1.20–1.40 (m, 10 H), 1.50–1.65 (m, 2 H), 1.80–1.95 (m, 2 H), 2.60–4.00(m, 10 H), 6.85–6.95(m, 3 H), 7.02 (d, J=9.0 Hz, 2 H), 7.20–7.35 (m, 2 H), 7.40 (d, J=9.0 Hz, 2 H), 7.45 (s, 1 H), 9.62 (brs, 1 H); MS (ES) m/z: 269.1 ((M+2H)$^{2+}$, 100%), 537.1(MH$^+$, 20%); HRMS Calcd. for C$_{30}$H$_{41}$N$_4$O$_3$S (MH$^+$): 537.2899. Found: 537.2875.

EXAMPLE 28

N-[5-((2R)-2-{1-[4-(2-Cyanoamino-4-oxo-4H-thiazol-5-ylidenemethyl)-phenyl]-piperidin-4-ylamino}-1-hydroxy-ethyl)-2-hydroxy-phenyl]-methanesulfonamide:

The title compound was prepared from 4-oxo-5-[4-(4-oxo-piperidin-1-yl)-benzylidene]-4,5-dihydro-thiazol-2-yl-cyanamide(which was obtained in Intermediate 36) and N-[5-(2-amino-(1R)-1-hydroxy-ethyl)-2-hydroxy-phenyl]-methanesulfonamide(which was obtained in Intermediate 10) according to the procedure of Example 1 as a yellowish solid; mp>300° C. (dec.); $^1$H NMR (300 MHz, DMSO-d$_6$) δ 1.40–1.60 (m, 10 H), 1.90–2.10 (m, 2 H), 2.70–3.00 (m, 3 H), 2.95(s, 3 H), 3.80–4.00 (m, 4 H), 4.67 (brd, J=7.2 Hz, 1 H), 6.81 (d, J=8.5 Hz, 1 H), 6.90–7.10 (m, 3 H), 7.23 (d, J=1.9 Hz, 1 H), 7.33 (s, 1 H), 7.40 (d, J=8.5 Hz, 2 H); MS (ES) m/z: 557.0(MH$^+$, 100%); HRMS Calcd. for C$_{25}$H$_{29}$N$_6$O$_5$S$_2$ (MH$^+$): 557.1641. Found: 557.1674.

EXAMPLE 29

(2S)-2-[5-(4-{4-[(2S)-2-Hydroxy-3-(2-oxo-2,3-dihydro-1H-benzoimidazol-4-yloxy)-propylamino]-piperidin-1-yl}-benzylidene)-4-oxo-4,5-dihydro-thiazol-2-ylamino]-pentanedioic acid:

The title compound was prepared from (2S)-2-{5-[4-(1,4-dioxa-8-aza-spiro[4.5]dec-8-yl)-benzylidene]-4-oxo-4,5-dihydro-thiazol-2-ylamino}-pentanedioic acid diethyl ester (which was obtained in Intermediate 34) and (S)-4-[2-hydroxy-3-aminopropoxy]-1,3-dihydro-2H-benzimidazol-2-one (Jesudason, C. D., et al., EP 0 764 640) according to the procedures of Intermediate 18, Example 1 and Example 9 as a yellowish solid; mp>270° C. (dec.); $^1$H NMR (300 MHz, DMSO-d$_6$) δ 1.40–1.70 (m, 2 H), 1.80–4.30 (m, 17 H), 6.50–6.80(m, 2 H), 6.80–7.10(m, 3 H), 7.23(d, J=8.4 Hz, 2 H), 7.37 (s, 1 H), 10.61(brs, 1 H), 11.01 (brs, 1 H); MS (ES) m/z: 320.3 ((M+2H)$^{2+}$, 100%); 639.4 (MH$^+$, 60%); HRMS Calcd. for C$_{30}$H$_{35}$N$_6$O$_8$S (MH$^+$): 639.2231. Found: 639.2233.

EXAMPLE 30

(2S)-2-[5-(4-{4-[(2R)-2-Hydroxy-2-(4-hydroxy-3-methanesulfonylamino-phenyl)-ethylamino]-piperidin-1-yl}-benzylidene)-4-oxo-4,5-dihydro-thiazol-2-ylamino]-pentanedioic acid diethyl ester:

The title compound was prepared from (2S)-2-{5-[4-(1,4-dioxa-8-aza-spiro[4.5]dec-8-yl)-benzylidene]-4-oxo-4,5-dihydro-thiazol-2-ylamino}-pentanedioic acid diethyl ester (which was obtained in Intermediate 34) and N-[5-(2-amino-(1R)-1-hydroxy-ethyl)-2-hydroxy-phenyl]-methanesulfonamide(which was obtained in Intermediate 10) according to the procedures of Intermediate 18 and Example 1 as a yellowish solid; mp>130° C. (dec.); $^1$H NMR (300 MHz, DMSO-d$_6$) δ 1.19(t, J=7.0 Hz, 3 H), 1.22(t, J=7.0 Hz, 3 H), 1.70–3.00 (m,14 H), 2.92(s, 3 H), 3.50–3.90 (m, 2 H), 4.05(q, J=7.0 Hz, 2 H), 4.14(q, J=7.0 Hz, 2 H), 4.48(dd, J=8.0, 4.3 Hz, 1 H), 4.68(dd, J=8.7, 5.4 Hz, 1 H), 6.82(d, J=8.2 Hz, 1 H), 7.02(dd, J=8.2, 2.0 Hz, 1 H), 7.05(d, J=8.9 Hz, 2 H), 7.18(d, J=2.0 Hz, 1 H), 7.40(d, J=8.9 Hz, 2 H), 7.50 (s, 1 H); MS (ES) m/z: 359.5 ((M+2H)$^{2+}$, 100%); 718.2 (MH$^+$, 20%); HRMS Calcd. for C$_{33}$H$_{44}$N$_6$O$_9$S$_2$ (MH$^+$): 718.2575. Found: 718.2581.

EXAMPLE 31

5-(4-{2-[(2S)-2-Hydroxy-3-(4-hydroxy-phenoxy)-propylamino]-ethoxy}-benzylidene)-2-piperidin-1-yl-thiazol-4-one hydrochloride salt:

The free base was prepared from [4-(4-oxo-2-piperidin-1-yl-4H-thiazo-5-ylidenemethyl)-phenoxy]-acetaldehyde hydrate (which was obtained in Intermediate 39) and (2S)-

1-amino-3-(4-hydroxy-phenoxy)-propan-2-ol (which was obtained in Intermediate 5) according to the procedures of Example 1. The free base was dissolved in methanol/dichloromethane and treated with hydrogen chloride gas. After concentrated the solvents the product was obtained as a yellowish solid; $^1$H NMR (300 MHz, DMSO-$d_6$) δ 1.50–1.70(m, 6 H), 3.00–4.50(m, 13 H), 6.69(d, J=8.9 Hz, 2 H), 6.78(d, J=8.9 Hz, 2 H), 7.13(d, J=8.6 Hz, 2 H), 7.60(s, 1 H), 7.62(d, J=8.6 Hz, 2 H), 8.92(brs, 1 H), 9.02 (brs, 1 H); MS (ES) m/z: 249.5 ((M+2H)$^{2+}$, 100%); 498.0 (MH$^+$, 20%); HRMS Calcd. for $C_{26}H_{32}N_3O_5S$ (MH$^+$): 498.2063. Found: 498.2039.

EXAMPLE 32

5-{4-[2-((2S)-2-Hydroxy-3-phenoxy-propylamino)-ethoxy]-benzylidene}-2-piperidin-1-yl-thiazol-4-one hydrochloride salt:

The title compound was prepared from [4-(4-oxo-2-piperidin-1-yl-4H-thiazo-5-ylidenemethyl)-phenoxy]-acetaldehyde hydrate (which was obtained in Intermediate 39) and (2S)-1-amino-3-phenoxy-propan-2-ol(which was obtained in Intermediate 3) according to the procedures of Example 1 as a yellowish gum; $^1$H NMR (300 MHz, DMSO-$d_6$) δ 1.55–1.75(m, 6 H), 2.50–4.50(m, 13 H), 6.90–7.60 (m, 9 H), 8.94 (brs, 1 H), 9.22 (brs, 1 H); MS (ES) m/z: 241.5 ((M+2H)$^{2+}$, 100%); 482.0 (MH$^+$, 30%); HRMS Calcd. for $C_{26}H_{32}N_3O_4S$ (MH$^+$): 482.2114. Found: 482.2120.

EXAMPLE 33

N-[2-Hydroxy-5-(1-hydroxy-2-{2-[4-(4-oxo-2-piperidin-1-yl-4H-thiazol-5-ylidenemethyl)-phenoxy]-ethylamino}-ethyl)-phenyl]-methanesulfonamide:

The title compound was prepared from [4-(4-oxo-2-piperidin-1-yl-4H-thiazo-5-ylidenemethyl)-phenoxy]-acetaldehyde hydrate (which was obtained in Intermediate 39) and N-[5-(2-amino-1-hydroxy-ethyl)-2-hydroxy-phenyl]-methanesulfonamide (which was obtained in Intermediate 9) according to the procedures of Example 1 as a yellowish gum; $^1$H NMR (300 MHz, DMSO-$d_6$) δ 1.50–1.70(m, 6 H), 2.66(d, J=6.3 Hz, 2 H), 2.93 (s, 3 H), 2.95(t, J=5.4 Hz, 2 H), 3.55–3.65(m, 2 H), 3.85–3.95(m, 2 H), 4.01 (t, J=5.4 Hz, 2 H), 4.55(t, J=6.3 Hz, 1 H), 6.82(d, J=8.9 Hz, 2 H), 6.96(dd, J=8.3, 2.0 Hz, 1 H), 7.08(d, J=8.9 Hz, 2 H), 7.19(d, J=2.0 Hz, 1 H), 7.56(d, J=8.3 Hz, 1H), 7.58 (s, 1 H); MS (ES) m/z: 281.0 ((M+2H)$^{2+}$, 100%); 561.0 (MH$^+$, 70%); HRMS Calcd. for $C_{26}H_{33}N_4O_6S_2$ (MH$^+$): 561.1842. Found: 561.1836.

EXAMPLE 34

8-Hydroxy-5-((2S)-2-hydroxy-3-{2-[4-(4-oxo-2-piperidin-1-yl-4H-thiazol-5-ylidenemethyl)-phenoxy]-ethylamino}-propoxy)-3,4-dihydro-1H-quinolin-2-one:

The title compound was prepared from [4-(4-oxo-2-piperidin-1-yl-4H-thiazo-5-ylidenemethyl)-phenoxy]-acetaldehyde hydrate (which was obtained in Intermediate 39) and 5-((2S)-3-amino-2-hydroxy-propoxy)-8-hydroxy-3,4-dihydro-1H-quinolin-2-one (which was obtained in Intermediate 12) according to the procedures of Example 1 as a yellowish solid; mp>115° C. (dec.); $^1$H NMR (300 MHz, DMSO-$d_6$) δ 1.50–1.70(m, 6 H), 2.38(t, J=7.9 Hz, 2 H), 2.60–2.90 (m, 6 H), 2.95(t, J=5.4 Hz, 2 H), 3.50–4.00(m, 5 H), 4.10(t, J=5.4 Hz, 2 H), 5.15 (brs, 1 H), 6.44(d, J=8.8 Hz, 1 H), 6.68(d, J=8.8 Hz, 1 H), 7.07(d, J=8.8 Hz, 2 H), 7.58(d, J=8.8 Hz, 2 H), 7.59)s, 1 H), 8.70(s, 1 H), 9.20 (brs, 1 H); MS (ES) m/z: 284.0 ((M+2H)$^{2+}$, 100%); 567.0 (MH$^+$, 70%); HRMS Calcd. for $C_{29}H_{35}N_4O_6S$ (MH$^+$): 567.2277. Found: 567.2254.

What is claimed is:
1. A compound of formula I having the structure

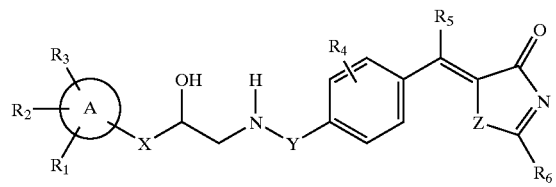

wherein:
A is aryl;
X is —OCH$_2$—, —SCH$_2$—, or a bond;
Y is alkyl of 1–6 carbon atoms, alkyloxy of 1–6 carbon atoms, azetidine, pyrrolidine or piperidine; wherein the nitrogen of the azetidine, pyrrolidine or piperidine is attached to the adjacent phenyl ring;
Z is S, O or NH with the proviso that when A is aryl, X is a bond and Y is piperidine, Z is not S;
$R_1$, $R_2$, and $R_3$ are each, independently, hydrogen, alkyl of 1–6 carbon atoms, cycloalkyl of 3–8 carbon atoms, hydroxy, halogen, trifluoromethyl, alkoxy of 1–6 carbon atoms, benzyloxy, allyloxy, propargyloxy, acyloxy of 2–7 carbon atoms, cyano, nitro, amino, aminocarbonyl, alkylamino of 1–6 carbon atoms, dialkylamino of 1–6 carbon atoms per alkyl group, formamido, ureido, acylamino of 2–7 carbon atoms, alkylsulfonylamino of 1–6 carbon atoms, arylsulfonylamino, dialkyloxyphosphorylamino of 1–6 carbon atoms per alkyl group, or dihydroxyphosphorylamino, or two of the three $R_1$, $R_2$ or $R_3$ substituents combine with the carbon to which each is attached to form a aryl fused cycloalkyl of 3–8 carbon atoms optionally substituted with an acylamino or hydroxy group;
$R_4$ is hydrogen, alkyl of 1–6 carbon atoms, alkoxy of 1–6 carbon atoms, hydroxy, carboxy, or halogen;
$R_5$ is hydrogen or alkyl of 1–6 carbon atoms;
$R_6$ is $NR_7R_8$;
$R_7$ and $R_8$ are taken together with the nitrogen to which each is attached to form a piperidinyl, piperazinyl or morpholinyl moiety optionally substituted with $R_9$;
$R_9$ is alkyl of 1–6 carbon atoms, cycloalkyl of 3–8 carbon atoms, arylalkyl having 1–6 carbon atoms in the alkyl group, hydroxy, halogen, trifluoromethyl, alkoxy of 1–6 carbon atoms, benzyloxy, allyloxy, propargyloxy, acyloxy of 2–7 carbon atoms, cyano, nitro, amino, aminocarbonyl, alkylamino of 1–6 carbon atoms, dialkylamino of 1–6 carbon atoms per alkyl group, formamido, ureido, acylamino of 2–7 carbon atoms, alkylsulfonylamino of 1–6 carbon atoms, arylsulfonylamino, dialkyloxyphosphorylamino of 1–6 carbon atoms per alkyl group, or dihydroxyphosphorylamino;
or a pharmaceutically acceptable salt thereof.
2. The compound of claim 1, wherein
A is a phenyl moiety or a napthyl moiety;
X is —OCH$_2$—, or a bond;
Y is alkyl of 1–6 carbon atoms, alkyloxy of 1–6 carbon atoms, or piperidine;
Z is S;
$R_1$, $R_2$, and $R_3$ are each, independently, hydrogen, alkyl of 1–6 carbon atoms, hydroxy, halogen, trifluoromethyl, alkoxy of 1–6 carbon atoms, acyloxy of 2–7 carbon atoms, cyano, nitro, amino, aminocarbonyl, alkylamino of 1–6 carbon atoms, dialkylamino of 1–6 carbon atoms per alkyl group, formamido, ureido, acylamino of 2–7 carbon atoms, or alkylsulfonylamino of 1–6 carbon atoms;

$R_4$ is hydrogen;

$R_5$ is hydrogen;

$R_6$ is $NR_7R_8$;

$R_7$ and $R_8$ are taken together with the nitrogen to which each is attached to form a piperidinyl moiety optionally substituted with $R_9$;

$R_9$ is alkyl of 1–6 carbon atoms, or arylalkyl having 1–6 carbon atoms in the alkyl group;

or a pharmaceutically acceptable salt thereof.

3. The compound of claim 1 wherein

A is phenyl;

X is a bond or —OCH$_2$—;

Y is alkyloxy of 1–6 carbon atoms or piperidine, with the proviso that when X is a bond, Y is not piperidine;

Z is S;

$R_1$, $R_2$, and $R_3$ are each, independently, hydrogen, alkyl of 1–6 carbon atoms, cycloalkyl of 3–8 carbon atoms, hydroxy, halogen, trifluoromethyl, alkoxy of 1–6 carbon atoms, benzyloxy, allyloxy, propargyloxy, acyloxy of 2–7 carbon atoms, cyano, nitro, amino, aminocarbonyl, alkylamino of 1–6 carbon atoms, dialkylamino of 1–6 carbon atoms per alkyl group, formamido, ureido, acylamino of 2–7 carbon atoms, alkylsulfonylamino of 1–6 carbon atoms, arylsulfonylamino, dialkyloxyphosphorylamino of 1–6 carbon atoms per alkyl group, or dihydroxyphosphorylamino, or two of the three $R_1$, $R_2$ or $R_3$ substituents combine with the carbon to which each is attached to form a aryl fused cycloalkyl of 3–8 carbon atoms optionally substituted with an acylamino or hydroxy group;

$R_4$ is hydrogen, alkyl of 1–6 carbon atoms, alkoxy of 1–6 carbon atoms, hydroxy, carboxy, or halogen;

$R_5$ is hydrogen or alkyl of 1–6 carbon atoms;

or a pharmaceutically acceptable salt thereof.

4. The compound of claim 1, which is a) N-[2-hydroxy-5-((2S)-2-hydroxy-3-{1-[4-(4-oxo-2-piperidin-1-yl-4H-thiazol-5-ylidenemethyl)-phenyl]-piperidin-4-ylamino}-propoxy)-phenyl]-methanesulfonamide;

b) 5-(4-{4-[(2S)-2-hydroxy-3-(4-hydroxy-phenoxy)-propylamino]-piperidin-1-yl}-benzylidene)-2-piperidin-1-yl-thiazol-4-one;

c) 5-{4-[4-((2S)-2-hydroxy-3-phenoxy-propylamino)-piperidin-1-yl]-benzylidene}-2-morpholin-4-yl-thiazol-4-one;

d) 5-(4-{4-[(2S)-2-hydroxy-3-(4-hydroxy-phenoxy)-propylamino]-piperidin-1-yl}-benzylidene)-2-morpholin-4-yl-thiazol-4-one;

e) 5-(4-{4-[(2S)-2-hydroxy-3-(4-hydroxy-phenoxy)-propylamino]-piperidin-1-yl}-benzylidene)-2-(4-methyl-piperazin-1-yl)-thiazol-4-one;

f) 5-(4-{2-[(2S)-2-hydroxy-3-(4-hydroxy-phenoxy)-propylamino]-ethoxy}-benzylidene)-2-piperidin-1-yl-thiazol-4-one;

g) 5-{4-[2-((2S)-2-hydroxy-3-phenoxy-propylamino)-ethoxy]-benzylidene}-2-piperidin-1-yl-thiazol-4-one; or h) N-[2-hydroxy-5-(1-hydroxy-2-{2-[4-(4-oxo-2-piperidin-1-yl-4H-thiazol-5-ylidenemethyl)-phenoxy]-ethylamino}-ethyl)-phenyl]-methanesulfonamide;

or a pharmaceutically acceptable salt thereof.

5. A pharmaceutical composition comprising:

a) at least one compound of formula I having the structure

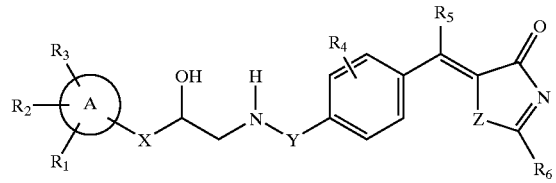

I wherein:

A is aryl;

X is —OCH$_2$—, —SCH$_2$—, or a bond;

Y is alkyl of 1–6 carbon atoms, alkyloxy of 1–6 carbon atoms, azetidine, pyrrolidine or piperidine; wherein the nitrogen of the azetidine, pyrrolidine or piperidine is attached to the adjacent phenyl ring;

Z is S, O or NH, with the proviso that when A is aryl, X is a bond and Y is piperidine, Z is not S;

$R_1$, $R_2$, and $R_3$ are each, independently, hydrogen, alkyl of 1–6 carbon atoms, cycloalkyl of 3–8 carbon atoms, hydroxy, halogen, trifluoromethyl, alkoxy of 1–6 carbon atoms, benzyloxy, allyloxy, propargyloxy, acyloxy of 2–7 carbon atoms, cyano, nitro, amino, aminocarbonyl, alkylamino of 1–6 carbon atoms, dialkylamino of 1–6 carbon atoms per alkyl group, formamido, ureido, acylamino of 2–7 carbon atoms, alkylsulfonylamino of 1–6 carbon atoms, arylsulfonylamino, dialkyloxyphosphorylamino of 1–6 carbon atoms per alkyl group, or dihydroxyphosphorylamino, or two of the three $R_1$, $R_2$ or $R_3$ substituents combine with the carbon to which each is attached to form a aryl fused cycloalkyl of 3–8 carbon atoms optionally substituted with an acylamino or hydroxy group;

$R_4$ is hydrogen, alkyl of 1–6 carbon atoms, alkoxy of 1–6 carbon atoms, hydroxy, carboxy, or halogen;

$R_5$ is hydrogen or alkyl of 1–6 carbon atoms;

$R_6$ is $NR_7R_8$;

$R_7$ and $R_8$ are taken together with the nitrogen to which each is attached to form a piperidinyl, piperazinyl or morpholinyl moiety optionally substituted with $R_9$;

$R_9$ is alkyl of 1–6 carbon atoms, cycloalkyl of 3–8 carbon atoms, arylalkyl having 1–6 carbon atoms in the alkyl group, hydroxy, halogen, trifluoromethyl, alkoxy of 1–6 carbon atoms, benzyloxy, allyloxy, propargyloxy, acyloxy of 2–7 carbon atoms, cyano, nitro, amino, aminocarbonyl, alkylamino of 1–6 carbon atoms, dialkylamino of 1–6 carbon atoms per alkyl group, formamido, ureido, acylamino of 2–7 carbon atoms, alkylsulfonylamino of 1–6 carbon atoms, arylsulfonylamino, dialkyloxyphosphorylamino of 1–6 carbon atoms per alkyl group, or dihydroxyphosphorylamino;

or a pharmaceutically acceptable salt thereof; and b) at least one pharmaceutical carrier.

* * * * *